(12) United States Patent
Butler et al.

(10) Patent No.: US 6,844,485 B2
(45) Date of Patent: Jan. 18, 2005

(54) NUCLEIC ACIDS ENCODING A PHYTOCHELATIN SYNTHASE AND USES THEREOF

(75) Inventors: Karlene H. Butler, Newark, DE (US); Omolayo O. Famodu, Newark, DE (US); Leslie T. Harvell, Newark, DE (US); Emil M. Orozco, Jr., Cochranville, PA (US); Sonriza Rasco-Gaunt, Wilmington, DE (US); Catherine J. Thorpe, Hampshire (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/214,269

(22) Filed: Aug. 7, 2002

(65) Prior Publication Data

US 2003/0114655 A1 Jun. 19, 2003

Related U.S. Application Data

(60) Provisional application No. 60/310,521, filed on Aug. 7, 2001.

(51) Int. Cl.$^7$ .................. C12N 15/09; C12N 15/29; C12N 15/82; A01H 5/00; A01H 5/10
(52) U.S. Cl. .................. 800/278; 800/298; 800/295; 435/468; 435/320.1; 435/430; 435/69.1; 536/23.2; 536/23.6
(58) Field of Search .................. 800/278, 298, 800/295; 435/468, 69.1, 320.1, 430, 419; 536/23.2, 23.6

(56) References Cited

U.S. PATENT DOCUMENTS 6,489,537 B1    12/2002   Rea et al.

OTHER PUBLICATIONS

Ouariti, O. et al., Cadmium–and Copper–Induced Changes in Tomato Membrane Lipids, *Phytochemistry*, 45 (7):1343–1350 (1997).

Dykema, P. et al., A New Class of Proteins Capable of Binding Transition Metals, *Plant Molecular Biology* 41:139–150 (1999).

Guerinot, M.L., The ZIP Family of Metal Transporters, *Biochim. Biophys Acta* 1465:190–198 (2000).

Rogers, E. et al., Altered Selectivity in an Arabidopsis Metal Transporter, *Proc. Natl. Acad. Sci. USA*, 97:12356–12360 (2000).

Vatamaniuk, O. et al., Mechanism of Heavy Metal Ion Activation of Phytochelatin (PC) Synthase, *J. Biol. Chem.*, 275 (40): 31451–31459 (2000).

Ha, S.B. et al., Phytochelatin Synthase Genes from Arabidopsis and the Yeast *Schizosaccharomyces prombe*, The *Plant Cell*, 11:1153–1163 (1999).

Clemens, S. et al., Tolerance to Toxic Metals by a Gene Family of Phytochelatin Synthases from Plants and Yeast, *EMBO J.*, 18(12):3325–3333 (1999).

Vatamaniuk, O., et al., AtPCS1, A Phytochelatin Synthase from Arabidopsis: Isolation and In Vitro Reconstitution, *Proc. Natl. Acad. Sci. USA*, 96:7110–7115 (1999).

Vatamaniuk, O., et al., A New Pathway for Heavy Metal Detoxification in Animals, *J. Biol. Chem.*, 276 (24):20817–20820 (2001).

NCBI General Identification No. 17024112, Nov. 29, 2001.

NCBI General Identification No. 5757804, Aug. 23, 1999.

NCBI General Identification No. 5305736, Aug. 14, 2000.

NCBI General Identification No. 18699092, Feb. 18, 2002.

Oven, M. et al., Molecular Characterization of the Homo–phytochelatin Synthase of Soybean *Glycine max, J. Biol. Chem.*, 277 (7):4747–4754 (2002).

*Primary Examiner*—Medina A. Ibrahim

(57) ABSTRACT

The present invention relates to isolated nucleic acids encoding a polypeptide having phytochelatin synthase activity. The invention also relates to recombinant DNA constructs comprising said nucleic acids; host cells transformed with said recombinant DNA constructs, and a method for producing recombinant phytochelatin synthase in said transformed host cells.

11 Claims, 3 Drawing Sheets

```
                  *       *****   *** ***    ** *        *  *    *  ******* ***
SEQ ID NO:12    1 MTTTMATIYRRVLPSPPAIDFVSSQGKQLFMEATQGGTMEGFFKLISYFQTQSEPAYCGL
SEQ ID NO:14    1 MAAAVASLYRRVLPSPPAVDFASPEGKRLFAEALAAGTMEGFFPLVSVFQTQSEPAFCGL
SEQ ID NO:16    1 MAA-MASLYRRVLPSPPAVEFASEEGKRLFSEALESGTLQGFFNLISVFQTQSEPAFCGL
SEQ ID NO:18    1 MAS--PGLYRRVLPSPS-IEFASPEGKKLFGEALERGTMQGFFKLISYYQTQSEPAYCGL
SEQ ID NO:19    1 ME--VASLYRRVLPSPPAVEFASAEGKRLFAEALQGGTMEGFFNLISYFQTQSEPAFCGL
SEQ ID NO:20    1 M--AMASLYRRSLPSPPAIDFSSAEGKLIFNEALQKGTMEGFFRLISYFQTQSEPAYCGL
                                                                             60

* * *****  * ***** ********************** *     *   *      *  **
SEQ ID NO:12   61 ATLAMVLNALSIDPGRKWKGPWRWFDESMLDCCEPLETVKAKGISFGKVVCLAHCAGAKV
SEQ ID NO:14   61 ASLAVVLNALAIDPGRRWKGPWRWFDESMLDCCEPLDKVKAEGITFGKVACLAHCSGADV
SEQ ID NO:16   60 ASLSVVLNALAIDPGRQWKGPWRWFDESMLDCCEPLDKVKAEGITFAKLACLAHCAGANV
SEQ ID NO:18   58 ATLSVVLNALAIDPGRKWKGPWRWFDESMLDCCEPLAKVKLEGITFGKVACLARCNGAKV
SEQ ID NO:19   59 ASLSVVLNALAIDPGRPWKGPWRWFDESMLDCCEPLHKVKAEGITEGKVVCLAHCAGARV
SEQ ID NO:20   59 ASLSVVLNALSIDPGRKWKGPWRWFDESMLDCCEPLEVVKEKGISFGKVVCLAHCSGAKV
                                                                             120

*      *   *     *   **   *   *  *     ***  * *** *** *  ***
SEQ ID NO:12  121 EAFRTNQTSIDEFRKHVVACSSSDDCHVIASYNRATFKQTGAGHFSPIGGYHAGRDMVLI
SEQ ID NO:14  121 QSFRTNRVTIHDLRRHLIRCVSSQDCHLIASYHRRPFGQTGTGHFSPIGGYHAGQDMVLI
SEQ ID NO:16  120 RSFRADQSTIHDFRHHLVRSASSQDCHLIASYHRKPFKQTGTGHFSPIGGYHAGQDMALI
SEQ ID NO:18  118 EAFRSDQSSVDDFRNRVISCSSSEDCHVIVSYHRTPLNQTGIGHFSPVGGYHAERDMVLV
SEQ ID NO:19  119 QSFRADQTTIHDFRAHLTRCASSQDCHLISSYHRSPFKQTGTGHFSPIGGYHAEKDMALI
SEQ ID NO:20  119 EAFRTSQSTIDDFRKFVVKCTSSENCHMISTYHRGVFKQTGTGHFSPIGGYNAERDMALI
                                                                             180
```

FIG. 1A

```
SEQ ID NO:12   181  LDVARFKYPPHWVPLKLLWEAMDTVDQASGYHRGFMLVSRLQRPPALLYTLSCKHESWVN
SEQ ID NO:14   181  LDVARFKYPPHWVPLQLLWEAMNTTDDSTGLLRGFMLISRKVAAPSLLYTVSCRDENWKR
SEQ ID NO:16   180  LDVARFKYPPHWVPLPLLWEAMNTTDDATGLLRGFMLISRHTAAPSLLYTVSCRDESWKS
SEQ ID NO:18   178  LDVARFKYPPHWVPLTLLWEGMSTIDQATRLRRGYMISRLNRAPSILYTVSCRHEGWSS
SEQ ID NO:19   179  LDVARFKYPPHWVPLTLLWDAMNTTDEATGLLRGFMLVSRRSSAPSLLYTVSCGHGSWKS
SEQ ID NO:20   179  LDVARFKYPPHWVPLKLLWEAMDSIDQSTGKRRGFMLISRPHREPGLLYTLSCKDESWIE
                                                                                240

SEQ ID NO:12   241  IAKYLTEDVPELLSSKNVKDVKDVLSIVFSSLPSKFLEFITWVPEVRRTEEGDQSLTPEE
SEQ ID NO:14   241  MSKYCVEDLPSLLKAGNLDDVPALLSRLIESLPADAESLIKWVEVRRKEEGGPSLNKEE
SEQ ID NO:16   240  MAKYCMEDVPDLLKDESVDNVPALLSRLVKSLPANAGNLIKWVIEVRRQEEGGSGLSKEE
SEQ ID NO:18   238  VAKFLTEDVPQLLKSEDLKDIQEVLSLAFKSPPSELRGLITWIAEVRRQEDGNLTLSEEE
SEQ ID NO:19   239  MAKYCVEDVPNLLKDESLDNVTTLLSRLVESLPANAGDLIKCVIEVRRKEEGESSLSKEE
SEQ ID NO:20   239  IAKYLKEDVPRLVSSQHVDSVEKIISVVFKSLPSNFNQFIRWVAEIRITEDSNQNLSAEE
                                                                                300

SEQ ID NO:12   301  QERLSIKGEILKQVQETELYKYVAD--FLDSPC------SGQEASLTEIAASVCCQGAGF
SEQ ID NO:14   301  KERLFLKENVLKQVRDTRLFAIVHDLQYANKPCYNC-SSPSEDDSLTRIAAVVCCQGAAM
SEQ ID NO:16   300  EERLILKEMILQQVRDTELFRLVRELQFTKQPCCSC-SYSSDDDSFTRIAASVCCQGAAL
SEQ ID NO:18   298  KGRLAIKADILEQIRTTGLFKHVTRWLDSESSCCNTLANLGDKDMLPALAASVCCQAADL
SEQ ID NO:19   299  KERLFLKEKVLQQIRDTDLFRVVHELQYPKGLCGSC-SSSSDEDSLAEIAATVCCQGAAF
SEQ ID NO:20   299  KSRLKLKQLVLKEVHETELEFKHINK--FLST------VGYEDSLTYAAAKACCQGAEI
                                                                                360

FIG. 1B
```

```
SEQ ID NO:12   353 LK--GNSESSDGFCCGETQVHCIKNNGAMPHVTIVSGTVTNGIGEQHVDMLVPSLTN---
SEQ ID NO:14   360 LS--GNLVPRDAFCCRETSFECVQANGD-GLKTVISGSVVCEGSEQGVDMLLPMSSPGAS
SEQ ID NO:16   359 LT--GNLSSKDGFCCRETCFKCVQVDGD-GPKTVVTGTAVSGVNEQSVDMLLPISTLETS
SEQ ID NO:18   358 LTVCGRLGLSGGKCCSQIDVKHLNADSENPVTLVSGIVTTGGGSEQGVDVLVPLCQREPS
SEQ ID NO:19   358 LS--GNLVSRDGFCCRETCIKCIEANGD-GLKTVISGTVVSKGNEQAVDLLPTSSSKTS
SEQ ID NO:20   349 LS--GS--PSKEFCCRETCVKCIKGPDD-SEGTVTGVVVRDGNEQKVDLLVPSTQTE--
                   361                                                       420

SEQ ID NO:12   408 ----------RIGLHPASSDVLIALLLALPPQIWSGIKDDTLLREIDTLVSMDNLPTLLQE
SEQ ID NO:14   417 -SCNSNLKSNAVKYPSSVDVLTVLLLALHPNTWLGIKDEKLKAEFQTLISTDSLPDDLKR
SEQ ID NO:16   416 -VCNSNSSNEVVKYPSRTDILTVLLLALHPSTWVGIKDERLKAEFQSLISTDILHDDLKR
SEQ ID NO:18   418 RLCLSNEGHCIGMHPSTADVLTVLLLALPLHTWSGIKEEKLRVEALSLLATEDLPPLLQE
SEQ ID NO:19   415 -LCNSNLKSKIVKYPSSTDVLTVLLLVLQPNTWLGIKDENVKAEFQSLVSTDNLPDLLKQ
SEQ ID NO:20   402 --CEC----GPEATYPAGNDVFTALLLALPPQTWSGIKDQALMHEMKQLISMASLPTLLQE
                   421                                                       480

SEQ ID NO:12   459 EVMHLRSQLYILKRCKDNELEKDLSAP-L---     486
SEQ ID NO:14   476 EILHLRRQLYYLKACKEEECEDAEQPSPKQQC     507
SEQ ID NO:16   475 EILHLRRQLHYVRSCKEEEYGDPVPQSH----     502
SEQ ID NO:18   478 EVLFLRDQLHFLMT-------DISAPS--PS     499
SEQ ID NO:19   474 EILHLRRQLHYLAGCKGQEACQEPPSP-----     500
SEQ ID NO:20   457 EVLHLRRQLQLLKRCQENKEEDDLAAPAY---     485
                   481                                  512
```

FIG. 1C

NUCLEIC ACIDS ENCODING A PHYTOCHELATIN SYNTHASE AND USES THEREOF

This application claims the benefit of U.S. Provisional Application No. 60/310,521, filed Aug. 7, 2001, the entire content of which is herein incorporated by reference.

FIELD OF THE INVENTION

This invention is in the field of plant molecular biology. More specifically, this invention includes nucleic acid fragments encoding phytochelatin synthase in plants and seeds.

BACKGROUND OF THE INVENTION

Metal ions such as magnesium, copper, zinc, manganese, nickel, and iron are essential for plant growth, in processes that range from respiration to photosynthesis, but deleterious when present in excess amounts. Others such as cadmium, aluminum, and lead have no nutritional value and are toxic. When present in large amount in the soil, metals interfere with the uptake of essential ions, biosynthesis of chlorophyll and nucleic acids, and lipid metabolism, thus profoundly affecting plant growth and development (Ouariti et al. (1997) *Phytochemistry* 45:1343–1350; Dykema et al. (1999) *Plant Mol Biol* 41:139–150).

With the necessity to regulate metal ion uptake and achieve metal ion homeostasis, plants have evolved a series of metal transporters and various metal-binding polypeptides and proteins. Metallothioneins and phytochelatins are intracellular sulfur-rich low molecular weight polypeptides that chelate metal ions such as cadmium, zinc, copper, and mercury, and are thought to play a role in detoxification. More recently, a group of metal transporters, the ZIP gene family, was identified in plants (Guerinot (2000) *Biochim Biophys Acta* 1465:190–198). IRT1, the first ZIP gene to be identified, encodes a protein that is able to transport iron, zinc, manganese, and cadmium (Rogers et al. (2000) *Proc Natl Acad Sci USA* 97:12356–12360).

A novel class of polypeptides that are capable of being isoprenylated and binding metal ions such as copper, nickel, and zinc has also been recently discovered (Dykema et al. (1999) *Plant Mol Biol* 41:139–150). These proteins appear to be soluble, unlike most isoprenylated proteins which are membrane-associated. In terms of structure, they share the CXXC metal-binding motifs, and contain repetitive regions rich in the amino acids Pro, Lys, Asp, Glu, and Gly, predicted to form alpha-helices. Preceding the carboxyl-terminus is a flexible region of 30–70 amino acids enriched in the amino acids Pro, Ala, Tyr, and Gly, predicted to form turns (Dykema et al. (1999) *Plant Mol Biol* 41:139–150). The eight amino acids proximal to the carboxyl-terminal isoprenylation CaaX motif are highly conserved, with a consensus sequence of FSDENPNA (SEQ ID NO:21) followed by the CaaX motif (Dykema et al. (1999) *Plant Mol Biol* 41:139–150).

Phytochelatins are a class of posttranslationally synthesized peptides ((γ-Glu-Cys)$_n$-Xaa polymers, where n is 2–11) whose synthesis from glutathione is promoted by heavy metals. They bind heavy metals such as cadmium with high affinity and localize themselves bound with the heavy metal ions to the cell vacuoles, thus playing a role in detoxification. Their synthesis is mediated by the enzyme phytochelatin synthase (γ-glutamylcysteine dipeptidyltranspeptidase, EC 2.3.2.15) using glutathione and related thiol tripeptides as substrate, via the net transfer of a γ-Glu-Cys unit from one thiol peptide to another or to a pre-existing phytochelatin molecule. Phytochelatin synthase is activated by heavy metals, a reflection more of the enzyme's requirement for glutathione-like peptides containing blocked thiol groups for activity, rather than direct metal binding to the enzyme (Vatamaniuk et al. (2000) *J Biol Chem* 275:31451–31459). Nucleic acid fragments encoding phytochelatin synthase have been isolated from *Arabidopsis*, yeast, wheat, and worm (Ha et al. (1999) *Plant Cell* 11:1153–1163; Clemens et al. (1999) *EMBO J.* 18:3325–3333; Vatamaniuk et al. (1999) *Proc Natl Acad Sci USA* 96:7110–7115; Vatamaniuk et al. (2000) *J Biol Chem* 275:31451–31459; Vatamaniuk et al. (2001) *J Biol Chem* 276:20817–20820).

It is apparent that by manipulating phytochelatin synthase expression, phytochelatin levels may be controlled, and consequently, heavy metal detoxification and tolerance by plants as well. Increasing phytochelatin synthase expression may lead to increased heavy (transition) metal resistance which has a potential use as a selectable marker system for plant transformation studies. Also, plants may be engineered to grow in toxic metal rich soils or to remove pollutant metals from the environment through manipulating expression of phytochelatin synthase. Accordingly, the instant specification discloses nucleotide sequences encoding phytochelatin synthase which may be used for the above mentioned applications.

SUMMARY OF THE INVENTION

The present invention concerns isolated polynucleotides comprising a nucleotide sequence encoding a polypeptide having phytochelatin synthase activity, wherein the amino acid sequence of the polypeptide and the amino acid sequence of SEQ ID NOs:2, 12, 14, 16 or 18 have at least 70% sequence identity. It is preferred that the identity be at least 80%, it is more preferred that the identity is at least 85%, it is even more preferred that the identity be at least 90%, it is even more preferred that the identity be at least 95%. The present invention also relates to isolated polynucleotides comprising the complement of the nucleotide sequence. More specifically, the present invention concerns isolated polynucleotides encoding the polypeptide sequence of SEQ ID NOs: 2, 12, 14, 16 or 18 or nucleotide sequences comprising the nucleotide sequence of SEQ ID NOs:1, 11, 13, 15 or 17.

In a first embodiment, the present invention relates to an isolated polynucleotide comprising: (a) a first nucleotide sequence encoding a first polypeptide having phytochelatin synthase activity, wherein the amino acid sequence of the first polypeptide and the amino acid sequence of SEQ ID NO:12 or SEQ ID NO:18 have at least 70% sequence identity based on the ClustalV alignment method, (b) a second nucleotide sequence encoding a second polypeptide having phytochelatin synthase activity, wherein the amino acid sequence of the second polypeptide and the amino acid sequence of SEQ ID NO:14 or SEQ ID NO:16 have at least 80% sequence identity based on the ClustalV alignment method, or (c) the complement of the nucleotide sequence of (a) or (b). The polypeptide preferably comprises the amino acid sequence of SEQ ID NO:12, 14, 16 or 18. The nucleotide sequence preferably comprises the nucleotide sequence of SEQ ID NOs:11, 13, 15 or 17. The polypeptide preferably has phytochelatin synthase activity.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention concerns a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a fifth embodiment, the present invention relates to a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a sixth embodiment, the present invention concerns a first nucleotide sequence which contains at least 30 nucleotides, and wherein the first nucleotide sequence is comprised by another polynucleotide, wherein the other polynucleotide includes: (a) a second nucleotide sequence, wherein the second nucleotide sequence encodes a polypeptide having phytochelatin synthase activity, wherein the amino acid sequence of the polypeptide and the amino acid sequence of SEQ ID NOs:2, 12, 14, 16, or 18 having at least 80%, 85%, 90%, or 95% sequence identity, or (b) the complement of the second nucleotide sequence of (a).

In a seventh embodiment, the present invention relates to an isolated polypeptide comprising an amino acid sequence having phytochelatin synthase activity, wherein the polypeptide comprises: (a) a first amino acid sequence, wherein the first amino acid sequence and the amino acid sequence of SEQ ID NO:12 or SEQ ID NO:18 have at least 70% sequence identity based on the ClustalV alignment method, or (b) a second amino acid sequence, wherein the second amino acid sequence and the amino acid sequence of SEQ ID NO:14 or SEQ ID NO:16 have at least 80% sequence identity based on the ClustalV alignment method. The first amino acid sequence preferably comprises the amino acid sequence of SEQ ID NOs:12 or 18, and the second amino acid sequence preferably comprises the amino acid sequence of SEQ ID NOs:14 or 16.

In an eight embodiment, the invention concerns a method for isolating a polypeptide encoded by the polynucleotide of the present invention comprising isolating the polypeptide from a cell containing a recombinant DNA construct comprising the polynucleotide operably linked to at least one regulatory sequence.

In a ninth embodiment, this invention relates to a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the phytochelatin synthase polynucleotide in an amount sufficient to complement a null mutant to provide a positive selection means.

In a tenth embodiment, this invention concerns a method of altering the level of expression of a phytochelatin synthase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the phytochelatin synthase protein in the transformed host cell.

In an eleventh embodiment, this invention relates to a method for positive selection of a transformed cell comprising: (a) transforming a host cell, preferably a plant cell, such as a monocot or a dicot, with the recombinant DNA construct of the present invention or an expression cassette of the present invention; (b) exposing the transformed host cell to toxic or growth-inhibitory levels of metal ions, and (c) growing the transformed host cell under conditions which allow expression of the phytochelatin synthase polynucleotide in an amount sufficient to overcome the negative effects of metal ion exposure and provide a positive selection means.

BRIEF DESCRIPTION OF THE DRAWINGS AND SEQUENCE LISTING

The invention can be more fully understood from the following detailed description and the accompanying drawings and Sequence Listing which form a part of this application.

FIGS. 1A, 1B and 1C depict the amino acid sequence alignment of the following phytochelatin synthases: (a) SEQ ID NO:12, encoded by the nucleotide sequence derived from sunflower clone hss1c.pk019.p5 (SEQ ID NO:11), (b) SEQ ID NO:14, encoded by the nucleotide sequence corresponding to a contig (SEQ ID NO:13) of sequences derived from corn clones cpi1c.pk022.m11 (SEQ ID NO:1) and p0031.ccmbg14r (SEQ ID NO:3), (c) SEQ ID NO:16, encoded by the nucleotide sequence corresponding to a contig (SEQ ID NO:15) of sequences derived from rice clone rlsu0c.pk005.f18 (SEQ ID NO:7) and PCR fragment sequence, (d) SEQ ID NO:18, encoded by the nucleotide sequence corresponding to a contig (SEQ ID NO:17) of sequences derived from soybean clone sgs4c.pk002.g1 (SEQ ID NO:9), PCR fragment sequence and a published soybean EST sequence (NCBI General Identifier (GI) No. 17024112), (e) SEQ ID NO:19, from *Triticum aestivum* (NCBI GI No. 5757804) and (f) SEQ ID NO:20, from *Arabidopsis thaliana* (NCBI GI No. 5305736). Amino acids which are conserved among all and at least two sequences with an amino acid at that position are indicated with an asterisk (*). Dashes are used by the program to maximize alignment of the sequences. The consensus amino acid sequence is numbered below the alignment. The amino acid residues for each SEQ ID NO are given to the left of each line of sequence, and to the right of the last line of sequence.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more EST, FIS or PCR fragment sequences ("Contig"), or sequences encoding the entire protein or functionally active polypeptide derived from an FIS or a contig ("CGS"). The sequence descriptions and Sequence Listing attached hereto comply with the rules governing nucleotide and/or amino acid sequence disclosures in patent applications as set forth in 37 C.F.R. §1.821–1.825.

TABLE 1

Phytochelatin Synthase

| Plant | Clone Designation | Status | SEQ ID NO: (Nucleotide) | SEQ ID NO: (Amino Acid) |
|---|---|---|---|---|
| Corn | cpi1c.pk022.m11 (FIS) | CGS | 1 | 2 |
| Corn | p0031.ccmbg14r | FIS | 3 | 4 |
| Rice | rca1n.pk015.j16 | FIS | 5 | 6 |
| Rice | rlsu0c.pk005.f18 | FIS | 7 | 8 |
| Soybean | sgs4c.pk002.g1 | FIS | 9 | 10 |
| Sunflower | hss1c.pk019.p5 (FIS) | CGS | 11 | 12 |
| Corn | Contig of: cpi1c.pk022.m11 (FIS) p0031.ccmbg14r (FIS) | CGS | 13 | 14 |
| Rice | Contig of: rlsu0c.pk005.f18 (FIS) PCR fragment sequence | CGS | 15 | 16 |
| Soybean | Contig of: sgs4c.pk002.g1 (FIS) PCR fragment sequence GI No. 17024112 | CGS | 17 | 18 |

SEQ ID NO:19 corresponds to the amino acid sequence of phytochelatin synthase from *Triticum aestivum* (NCBI GI No. 5757804).

SEQ ID NO:20 corresponds to the amino acid sequence of phytochelatin synthase from *Arabidopsis thaliana* (NCBI GI No. 5305736).

The Sequence Listing contains the one letter code for nucleotide sequence characters and the three letter codes for amino acids as defined in conformity with the IUPAC-IUBMS standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The problem to be solved, therefore, was to identify polynucleotides that encode phytochelatin synthase proteins. These polynucleotides may be used in plant cells to alter metal ion accumulation in plants. More specifically, the polynucleotides of the instant invention may be used to create transgenic plants where the phytochelatin synthase levels are altered with respect to non-transgenic plants which would result in plants with increased heavy (transition) metal resistance which has a potential use as a selectable marker system for plant transformation studies. Also, plants may be engineered to grow in toxic metal rich soils or to remove pollutant metals from the environment through manipulating expression of phytochelatin synthase. The present invention provides polynucleotide and deduced polypeptide sequences corresponding to novel phytochelatin synthase genes from corn (*Zea mays*), rice (*Oryza sativa*), soybean (*Glycine max*) and sunflower (Helianthus sp.).

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7, 9, 11, 13, 15 or 17, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence. The term "recombinant DNA construct" also embraces an isolated polynucleotide comprising a region encoding all or part of a functional RNA and at least one of the naturally occurring regulatory sequences directing expression in the source (e.g., organism) from which the polynucleotide was isolated, such as, but not limited to, an isolated polynucleotide comprising a nucleotide sequence encoding a phytochelatin synthase and the corresponding promoter and 3' end sequences directing expression in the source from which sequences were isolated.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs:1, 3, 5, 7, 9, 11, 13, 15 or 17, and the complement of such nucleotide sequences may be used to affect the expression and/or function of a phytochelatin syntase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) *CABIOS.* 5:151–153) with the default parameters (GAP PENALTY=10, GAP LENGTH PENALTY=10). Default parameters for pairwise alignments using the ClustalV method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a recombinant DNA construct that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632). A "mitochondrial signal peptide" is an amino acid sequence which directs a precursor protein into the mitochondria (Zhang and Glaser (2002) Trends Plant Sci 7:14–21).

"Transformation" refers to the transfer of a nucleic acid fragment into the genome of a host organism. Host organisms containing the transferred nucleic acid fragments are referred to as "transgenic" or "transformed" organisms. Examples of methods of plant transformation include Agrobacterium-mediated transformation (De Blaere et al. (1987) Meth. Enzymol. 143:277; Ishida Y. et al. (1996) Nature Biotech. 14:745–750) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" or "transformed" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence encoding a phytochelatin syntase polypeptide having at least 70% or 80% sequence identity, based on the ClustaIV method of alignment, when compared to a polypeptide of SEQ ID NOs:2, 4, 6, 8, 10, 12, 14, 16 or 18.

This invention also relates to the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several phytochelatin synthase protein have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other phytochelatin synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs:1, 3, 5, 7, 9, 11, 13, 15 or 17, and the complement of such nucleotide sequences, may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of phytochelatin synthase in those cells. It is apparent that by manipulating phytochelatin synthase expression, phytochelatin levels may be controlled, and consequently, heavy metal detoxification and tolerance by plants as well. Increasing phytochelatin synthase expression may lead to increased heavy (transition) metal resistance which has a potential use as a selectable marker system for plant transformation studies. Also, plants may be engineered to grow in toxic metal rich soils or to remove pollutant metals from the environment through increased expression of phytochelatin synthase. Accordingly, the instant specification discloses nucleotide sequences encoding phytochelatin synthase which may be used for the above mentioned applications.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. Non-coding 3' sequences comprising transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) EMBO J. 4:2411–2418; De Almeida et al. (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell (Economou (1999) Trends Microbiol. 7:315–320; Fernandez et al. (2000) Appl. Environ. Microbiol. 66:5024–5029; Kjeldsen et al. (2002) J. Biol. Chem. 277:18245–18248; U.S. Pat. No. 6,348,344). It is thus envisioned that the recombinant DNA construct(s) described above may be further supplemented by directing the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), nuclear localization signals (Raikhel (1992) Plant Phys. 100:1627–1632) or mitochondrial signal sequences (Zhang and Glaser (2002) Trends Plant Sci 7:14–21) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a phytochelatin synthase polypeptide having an amino acid sequence that is at least 70 or 80% identical, based on the ClustalV method of alignment, to a polypeptide of SEQ ID NOs: 2, 4, 6, 8, 10, 12, 14, 16 or 18.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded phytochelatin synthase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:3741. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*), rice (*Oryza sativa*), soybean (*Glycine max*), and sunflower (Helianthus sp.) tissues were prepared. The characteristics of the libraries are described below.

TABLE 2 cDNA Libraries from Corn, Rice, Soybean, and Sunflower

| Library | Tissue | Clone |
|---|---|---|
| cpi1c | Corn Treated with Chemicals Related to Biochemical Compound Synthesis* | cpi1c.pk022.m11 |
| hss1c | Sclerotinia Infected Sunflower Plant | hss1c.pk019.p5 |
| p0031 | Corn Shoot Culture | p0031.ccmbg14r |
| rca1n | Rice Callus** | rca1n.pk015.j16 |

TABLE 2-continued cDNA Libraries from Corn, Rice, Soybean, and Sunflower

| Library | Tissue | Clone |
| --- | --- | --- |
| rlsu0c | Rice Leaf | rlsu0c.pk005.f18 |
| sgs4c | Soybean Seed 2 Days After Germination | sgs4c.pk002.g1 |

*Chemicals used included sorbitol, egosterol, taxifolin, methotrexate, D-mannose, D-galactose, alpha-amino adipic acid, and ancymidol, all of which are commercially available from Calbiochem-Novabiochem Corp. (1-800-628-8470).
**This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding phytochelatin synthases were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Phytochelatin Synthase

The BLASTX search using the EST sequences from clones listed in Table 3 revealed similarity of the polypeptides encoded by the cDNAs to phytochelatin synthases from *Triticum aestivum* (NCBI General Identifier (GI) No. 5757804; SEQ ID NO:19) and *Arabidopsis thaliana* (NCBI GI No. 5305736; SEQ ID NO:20). Shown in Table 3 are the BLAST results for individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire protein, or functionally active polypeptide, derived from an EST, FIS or a contig ("CGS"):

TABLE 3

BLAST Results for Sequences Encoding Polypeptides Homologous to Phytochelatin Synthase

| Clone | Status | BLAST Results | |
|---|---|---|---|
| | | NCBI GI No. | pLog Score |
| cpi1c.pk022.m11 (FIS) | CGS | 5757804 | >180.00 |
| p0031.ccmbg14r | FIS | 5757804 | 93.10 |
| rca1n.pk015.j16 | FIS | 5757804 | 27.70 |
| rlsu0c.pk005.f18 | FIS | 5757804 | 159.00 |
| sgs4c.pk002.g1 | FIS | 5757804 | 110.00 |
| hss1c.pk019.p5 (FIS) | CGS | 5305736 | >180.00 |

The cDNA insert in the clone, hss1c.pk019.p5, was found to encode the entire sunflower phytochelatin synthase gene (SEQ ID NO:11). The corresponding amino acid sequence, SEQ ID NO:12, is the open-reading frame encoded by nucleotides 106–1563 of SEQ ID NO:11.

A sequence alignment of the corn phytochelatin synthase sequence, SEQ ID NO:2, with the wheat phytochelatin synthase sequence, SEQ ID NO:19, indicated that SEQ ID NO:2 was missing approximately 32 amino acids relative to the wheat protein, at a position around 360 amino acids into the open-reading frame. A contig of SEQ ID NO:1 and SEQ ID NO:3 was assembled and is shown as SEQ ID NO:13. This contig contains a 93 nucleotide insert relative to the nucleotide sequence of SEQ ID NO:1, occurring between the two G residues at positions 1285 and 1286 of SEQ ID NO:1. The corresponding open-reading frame for SEQ ID NO:13, from nucleotides 202–1722, is given as SEQ ID NO:14. SEQ ID NO:14 contains 31 amino acids more that SEQ ID NO:2, and gives a better alignment (FIGS. 1A–1C) with the functionally active phytochelatin synthase from wheat (Clemens et al. (1999) EMBO J. 18:3325–3333). The 93 nucleotide insert in SEQ ID NO:13 begins with GT and ends with AG, the standard dinucleotides seen at the beginning and end of introns. SEQ ID NO:2 may represent an alternatively spliced (or aberrantly spliced) version of phytochelatin synthase from corn.

The sequence of the cDNA insert in rlsu0c.pk005.f18 was found not to encode the entire rice phytochelatin synthase. Consequently, PCR-based methods well known in the art and described in Example 1 were employed to obtain the entire coding sequence for a full-length rice phytochelatin synthase (SEQ ID NO:15). The corresponding open-reading frame for SEQ ID NO:15, from nucleotides 119–1624, is given as SEQ ID NO:16.

The sequence of the cDNA insert in sgs4c.pk002.g1 was found to encode a portion of the soybean phytochelatin synthase. The sequence of the insert in sgs4c.pk002.g1 is similar to amino acids 6–256 of the wheat phytochelatin synthase (SEQ ID NO:19). Consequently, PCR-based methods well known in the art and described in Example 1 were employed to obtain the missing 3' terminal sequence. The full-insert sequence of sgs4c.pk002.g1, PCR fragment sequence of the 3' end of the gene, and publically available soybean EST GI No. 17024112 were combined into a contig to obtain the complete gene sequence of the soybean phytochelatin synthase (SEQ ID NO:17). Soybean EST GI No. 17024112 contributed the first 67 nucleotides of SEQ ID NO:17. The corresponding 499 amino acid open-reading frame of SEQ ID NO:17, from nucleotides 53–1549, is given as SEQ ID NO:18.

Shown in Table 4 are the BLASTX results for the complete gene sequences of phytochelatin synthase from corn, rice and soybean. Table 4 shows the similarity of the polypeptides encoded by the corn, rice and soybean contigs, to the phytochelatin syntase from *Triticum aestivum* (NCBI GI No. 5757804; SEQ ID NO:19).

TABLE 4

BLAST Results for Sequences Encoding Polypeptides Homologous to Wheat Phytochelatin Synthase (NCBI GI No. 5757804)

| Sequence | Plant | Status | pLog Score |
|---|---|---|---|
| Contig of: cpi1c.pk022.m11 (FIS) p0031.ccmbg14r (FIS) | corn | CGS | >180 |

TABLE 4-continued

BLAST Results for Sequences Encoding
Polypeptides Homologous to Wheat
Phytochelatin Synthase (NCBI GI No. 5757804)

| Sequence | Plant | Status | pLog Score |
|---|---|---|---|
| Contig of:<br>rlsu0c.pk005.f18 (FIS)<br>PCR fragment sequence | rice | CGS | >180 |
| Contig of:<br>sgs4c.pk002.g1 (FIS)<br>PCR fragment sequence<br>GI No. 17024112 | soybean | CGS | 158 |

FIGS. 1A, 1B and 1C present an alignment of the amino acid sequences set forth in SEQ ID NOs:12, 14, 16, 18, 19 (wheat; GI No. 5757804), and 20 (Arabidopsis; GI No. 5305736). The data in Table 5 represents a calculation of the percent sequence identities of the amino acid sequences set forth in SEQ ID NOs:2, 12, 14, 16 and 18, when compared to the phytochelatin synthases from *Triticum aestivum* (NCBI GI No. 5757804; SEQ ID NO: 19) and *Arabidopsis thaliana* (NCBI GI No. 5305736; SEQ ID NO:20).

TABLE 5

Percent Identity of Amino Acid Sequences
Deduced from the Nucleotide Sequences
Encoding Polypeptides Homologous to
Phytochelatin Synthase

| Sequence | SEQ ID NO. | % Identity to GI No. 5757804 | % Identity to GI No. 5305736 |
|---|---|---|---|
| cpi1c.pk022.m11 (FIS) | 2 | 73.7 | 52.9 |
| hss1c.pk019.p5 (FIS) | 12 | 57.6 | 62.7 |
| Contig of:<br>cpi1c.pk022.m11 (FIS)<br>p0031.ccmbg14r (FIS) | 14 | 75.6 | 56.1 |
| Contig of:<br>rlsu0c.pk005.f18 (FIS)<br>PCR fragment sequence | 16 | 76.6 | 56.3 |
| Contig of:<br>sgs4c.pk002.g1 (FIS)<br>PCR fragment sequence<br>GI No. 17024112 | 18 | 53.3 | 52.6 |

Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) CABIOS. 5:151–153) with the default parameters (GAP PENALTY=10, GAP LENGTH PENALTY=10). Default parameters for pairwise alignments using the ClustalV method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode the complete phytochelatin synthase from corn, rice, soybean and sunflower. A sequence for a different phytochelatin synthase gene from soybean has recently been described (GI No. 18699092; Oven et al. (2002) *J. Biol. Chem.* 277:4747–4754). The soybean phytochelatin synthase of SEQ ID NO:18 has 56.4% sequence identity with the amino acid sequence of GI No. 18699092.

Example 4

Expression of Recombinant DNA Constructs in Monocot Cells

A recombinant DNA construct comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone, plant cDNA or plant cDNA libraries, using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML1 03 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptide, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone, plant cDNA or plant cDNA libraries, using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterum tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNA fragment of the gene may be generated by polymerase chain reaction (PCR) of the cDNA clone, plant cDNA or plant cDNA libraries, using appropriate oligonucleotide primers. The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 $\mu$g/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 $\mu$L of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-$\beta$-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

Example 7

Assaying for Phytochelatin Synthase Activity

The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include □-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond□ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For

Example 8

Expression of Recombinant DNA Constructs in Yeast Cells

The polypeptides encoded by the polynucleotides of the instant invention may be expressed in a yeast (Saccharomyces cerevisiae) strain YPH. Plasmid DNA, plant cDNA or plant cDNA libraries may be used as template to amplify the portion encoding the phytochelatin synthase. Amplification may be performed using the GC melt kit (Clontech) with a 1 M final concentration of GC melt reagent and using a Perkin Elmer 9700 thermocycler. The amplified insert may then be incubated with a modified pRS315 plasmid (NCBI General Identifier No. 984798; Sikorski, R. S. and Hieter, P. (1989) Genetics 122:19–27) that has been digested with Not I and Spe I. Plasmid pRS315 has been previously modified by the insertion of a bidirectional gal1/10 promoter between the Xho I and Hind III sites. The plasmid may then be transformed into the YPH yeast strain using standard procedures where the insert recombines through gap repair to form the desired transformed yeast strain (Hua, S. B. et al. (1997) Plasmid 38:91–96).

Yeast cells may be prepared according to a modification of the methods of Pompon et al. (Pompon, D. et al. (1996) Meth. Enz 272:51–64). Briefly, a yeast colony will be grown overnight (to saturation) in SG (-Leucine) medium at 30° C. with good aeration. A 1:50 dilution of this culture will be made into 500 mL of YPGE medium with adenine supplementation and allowed to grow at 30° C. with good aeration to an $OD_{600}$ of 1.6 (24–30 h). Fifty mL of 20% galactose will be added, and the culture allowed to grow overnight at 30° C. The cells will be recovered by centrifugation at 5,500 rpm for five minutes in a Sorvall GS-3 rotor. The cell pellet resuspended in 500 mL of 0.1 M potassium phosphate buffer (pH 7.0) and then allowed to grow at 30° C. for another 24 hours.

The cells may be recovered by centrifugation as described above and the presence of the polypeptide of the instant invention determined by HPLC/mass spectrometry or any other suitable method.

Example 9

Expression of Recombinant DNA Constructs in Insect Cells

The cDNA fragment of the gene may be generated by polymerase chain reaction (PCR) of the cDNA clone, plant cDNA or plant cDNA libraries, using appropriate oligonucleotide primers. The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of E. coli DH5α, isolated colonies are chosen and plasmid DNA is prepared and is analyzed by restriction enzyme analysis. Colonies containing the appropriate fragment are isolated, propagated, and plasmid DNA is prepared for cotransfection.

Spodoptera frugiperda cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), Baculovirus Expression Vectors: A Laboratory Manual, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large-scale propagation of recombinant viruses. Expression of the instant polypeptides encoded by the recombinant baculovirus is confirmed by any of the methods mentioned in Example 7.

---

What is claimed is:

1. An isolated polynucleotide comprising:
   (a) a nucleotide sequence encoding a polypeptide having phytochelatin synthase activity, wherein the polypeptide has an amino acid sequence of at least 95% sequence identity, based on the ClustalV alignment method with default pairwise alignment parameters of KTUPLE=1, GAP PENALTY=3, WINDOW=5 and DIAGONALS SAVED=5, when compared to SEQ ID NO:18, or
   (b) a complement of the nucleotide sequence of (a), wherein the complement and the nucleotide sequence consist of the same number of nucleotides and are 100% complementary.

2. The isolated polynucleotide of claim 1, wherein the amino acid sequence of the polypeptide comprises SEQ ID NO:18.

3. The isolated polynucleotide of claim 1, wherein the nucleotide sequence comprises SEQ ID NO:17.

4. A vector comprising the isolated polynucleotide of claim 1.

5. A recombinant DNA construct comprising the isolated polynucleotide of claim 1 operably linked to at least one regulatory sequence.

6. A method for transforming a host cell, comprising transforming a host cell with the isolated polynucleotide of claim 1.

7. A host cell comprising the recombinant DNA construct of claim 5.

8. A method for producing a polypeptide having phytochelatin synthase activity comprising: cultivating the host cell of claim 7 under conditions that allow for the synthesis of the polypeptide, and isolating the polypeptide from the cultivated host cell.

9. A method for producing a plant comprising transforming a plant cell with the isolated polynucleotide of claim 1 and regenerating a plant from the transformed plant cell.

10. A plant comprising the recombinant DNA construct of claim 5.

11. A seed comprising the recombinant DNA construct of claim 5.

* * * * *

SEQUENCE LISTING

<160> NUMBER OF SEQ ID NOS: 21

<210> SEQ ID NO 1
<211> LENGTH: 1927
<212> TYPE: DNA
<213> ORGANISM: Zea mays

<400> SEQUENCE: 1

```
gcacgagccg ggttctgtgg gctctcgtcc atcgtgcccg tcgtcgtctg cagagattcg      60
aaacgaaagt gagagagcat cgcagaggaa aggaggcacc cttcgctggc tcgatcgccg     120
ctgtgttcac gcggaggaac tagatcagca cgcgaaagcc aacagcgcag tcgaggagga     180
agcgagcagt ccaggtccag gatggcggcg gccgtggcgt cgctgtacag gcgggtcctc     240
ccgtcgccgc cggcggtgga cttcgcttcg ccggagggca agcgcctatt cgcggaggcc     300
```

-continued

```
ctggcggcgg gcaccatgga gggtttcttc ccctggtct ccgtcttcca gacgcagtcg    360
gagccggcct tctgcggcct ggcctccctt gccgtcgtgc tcaacgcgct cgccatcgac    420
ccgggccgcc gctggaaggg gccctggcgg tggttcgacg agtccatgct cgactgctgc    480
gagcccctcg ataaggtcaa ggccgagggc atcaccttcg gcaaggtcgc ctgtctcgcg    540
cactgctccg gagccgacgt ccaatccttc cgcaccaacc gggttaccat ccacgaccta    600
cggcggcatc tcatccgatg cgtctcctcg caggactgcc atctgatcgc tcctaccac    660 aggcggcctt tcggacagac tggaactggt catttctccc caattggtgg ctaccatgcc    720
ggacaggata tggtgctcat cttggatgtc gcccgtttca aatatcctcc gcattgggtt    780
ccattgcaac ttctttggga agccatgaat acaactgatg actcaactgg acttctcaga    840
gggttcatgc ttatatcaag aaaggttgca gccccttcat tgttgtacac agtgagttgc    900
agagatgaaa actggaaacg catgtcaaaa tattgtgttg aagatttacc gagtcttctg    960
aaggcaggga acctagacga tgttccagcg cttctgtccc gtttaattga gtctcttcca   1020
gctgacgctg aatctttgat caaatgggtt gtcgaagtca ggagaaaaga ggagggtgga   1080
ccaagcttaa acaagagga gaaagaaagg cttttcttga aggaaaatgt actaaagcaa   1140
gttcgtgata ccaggctatt tgccatagtc catgatttgc agtatgctaa taaaccatgt   1200
tataattgct catcgccgag cgaagatgat tcccttacta ggattgcagc cgttgtgtgc   1260
tgtcagggag ctgcaatgct atcaggctcc gtggtatgtg aaggcagtga acaaggtgtt   1320
gatatgcttt taccaatgtc ttcacctggt gccagttcat gcaattcaaa cttgaaaagc   1380
aatgccgtca aatatccatc aagcgtggat gttctaactg ttcttctgct ggctttacat   1440
cccaacacgt ggttgggcat caagacgag aagctgaaag ctgaatttca gactcttatt   1500
tcaacagaca gtttacctga tgatctgaaa cgagagatat tgcatctaag gcggcaactc   1560
tactatctaa aggcctgtaa agaagaggaa tgcgaagatg ccgagcaacc atcgcctaag   1620
cagcagtgct gaagtggcag tgtgcccatg tcgttagttt tacttgtaag aaattgatgt   1680
gaagggaaaa gttaccagag ggtatagact atgaaatggt cagaattatg atgatagtag   1740
tgtagtgatg attatcttgt tgttcagttc tggtgttgtt tccttctacg agaggctatt   1800
acaccctcct tgctcaagga ggtgctaatg ttctttttct agatgatgat taaaccatcc   1860
atccatcctt gcttgctttg tgctaaaaaa aaaaaaaaaa aaaaaaaaaa aaaaaaaaaa   1920
aaaaaaa                                                              1927
```

<210> SEQ ID NO 2
<211> LENGTH: 476
<212> TYPE: PRT
<213> ORGANISM: Zea mays

<400> SEQUENCE: 2

```
Met Ala Ala Ala Val Ala Ser Leu Tyr Arg Arg Val Leu Pro Ser Pro
 1               5                  10                  15

Pro Ala Val Asp Phe Ala Ser Pro Glu Gly Lys Arg Leu Phe Ala Glu
                20                  25                  30

Ala Leu Ala Ala Gly Thr Met Glu Gly Phe Phe Pro Leu Val Ser Val
            35                  40                  45

Phe Gln Thr Gln Ser Glu Pro Ala Phe Cys Gly Leu Ala Ser Leu Ala
        50                  55                  60

Val Val Leu Asn Ala Leu Ala Ile Asp Pro Gly Arg Arg Trp Lys Gly
 65                  70                  75                  80
```

-continued

```
Pro Trp Arg Trp Phe Asp Glu Ser Met Leu Asp Cys Cys Glu Pro Leu
                 85                  90                  95
Asp Lys Val Lys Ala Glu Gly Ile Thr Phe Gly Lys Val Ala Cys Leu
            100                 105                 110
Ala His Cys Ser Gly Ala Asp Val Gln Ser Phe Arg Thr Asn Arg Val
            115                 120                 125
Thr Ile His Asp Leu Arg Arg His Leu Ile Arg Cys Val Ser Ser Gln
        130                 135                 140
Asp Cys His Leu Ile Ala Ser Tyr His Arg Arg Pro Phe Gly Gln Thr
145                 150                 155                 160
Gly Thr Gly His Phe Ser Pro Ile Gly Gly Tyr His Ala Gly Gln Asp
                165                 170                 175
Met Val Leu Ile Leu Asp Val Ala Arg Phe Lys Tyr Pro Pro His Trp
            180                 185                 190
Val Pro Leu Gln Leu Leu Trp Glu Ala Met Asn Thr Thr Asp Asp Ser
        195                 200                 205
Thr Gly Leu Leu Arg Gly Phe Met Leu Ile Ser Arg Lys Val Ala Ala
210                 215                 220
Pro Ser Leu Leu Tyr Thr Val Ser Cys Arg Asp Glu Asn Trp Lys Arg
225                 230                 235                 240
Met Ser Lys Tyr Cys Val Glu Asp Leu Pro Ser Leu Lys Ala Gly
                245                 250                 255
Asn Leu Asp Asp Val Pro Ala Leu Leu Ser Arg Leu Ile Glu Ser Leu
            260                 265                 270
Pro Ala Asp Ala Glu Ser Leu Ile Lys Trp Val Glu Val Arg Arg
        275                 280                 285
Lys Glu Glu Gly Gly Pro Ser Leu Asn Lys Glu Lys Glu Arg Leu
290                 295                 300
Phe Leu Lys Glu Asn Val Leu Lys Gln Val Arg Asp Thr Arg Leu Phe
305                 310                 315                 320
Ala Ile Val His Asp Leu Gln Tyr Ala Asn Lys Pro Cys Tyr Asn Cys
                325                 330                 335
Ser Ser Pro Ser Glu Asp Ser Leu Thr Arg Ile Ala Ala Val Val
            340                 345                 350
Cys Cys Gln Gly Ala Ala Met Leu Ser Gly Ser Val Val Cys Glu Gly
        355                 360                 365
Ser Glu Gln Gly Val Asp Met Leu Leu Pro Met Ser Ser Pro Gly Ala
370                 375                 380
Ser Ser Cys Asn Ser Asn Leu Lys Ser Asn Ala Val Lys Tyr Pro Ser
385                 390                 395                 400
Ser Val Asp Val Leu Thr Val Leu Leu Ala Leu His Pro Asn Thr
                405                 410                 415
Trp Leu Gly Ile Lys Asp Glu Lys Leu Lys Ala Glu Phe Gln Thr Leu
            420                 425                 430
Ile Ser Thr Asp Ser Leu Pro Asp Asp Leu Lys Arg Glu Ile Leu His
        435                 440                 445
Leu Arg Arg Gln Leu Tyr Tyr Leu Lys Ala Cys Lys Glu Glu Glu Cys
450                 455                 460
Glu Asp Ala Glu Gln Pro Ser Pro Lys Gln Gln Cys
465                 470                 475

<210> SEQ ID NO 3
<211> LENGTH: 1027
```

<212> TYPE: DNA
<213> ORGANISM: Zea mays

<400> SEQUENCE: 3

```
ccacgcgtcc ggcgcttctg tcccgtttaa ttgagtctct tccagctgac gctgaatctt    60
tgatcaaatg ggttgtcgaa gtcaggagaa agaggaggg tggaccaagc ttaaacaaag    120
aggagaaaga aaggcttttc ttgaaggaaa atgtactaaa gcaagttcgt gataccaggc    180
tatttaccat agtccatgat tgcagtatg ctaataaacc atgttataat tgctcatcgt    240
cgagcgaaga tgattccctt actaggattg cagccgttgt gtgctgtcag ggagctgcaa    300
tgctatcagg taaccttgtg ccaagagatg ccttctgctg cagagaaaca agctttgaat    360
gtgtccaagc gaatggtgac gggcttaaga ctgttatctc aggctccgtg gtatgtgaag    420
gcagtgaaca aggtgttgat atgcttttac caatgtcttc acctggtgcc agttcatgca    480
attcaaactt gaagagcaat gccgtcaaat atccatcaag cgtggatgtt ctaactgttc    540
ttctgctggc tttacatccc aacacgtggt tgggcatcaa agacgagaag ctcaaagctg    600
aatttcagac tcttatttca acagacagtc tacctgatga tctgaaacga gagatattgc    660
acctaaggcg gcaactctac tatctaaagg cctgtaaaga gaggaatgc gaagatgccg    720
agcaaccatc gcctaagcag cagtgctgaa gtggcagtgt gcccatgtcg ttaattttac    780
ttgtaagaaa ttgatgtgaa gggaaaagtt accagagggt atagactatg aaatggtcag    840
aattatgatg atagtagtgt agtgatgatt atcttgttgt tcagttctgg tgttgtttcc    900
ttctacgaga ggctattaca ccctccttgc tcaaggaggg gctgatgttc tttttctaga    960
tgatgattaa accatccatc cttgctttgt gctaaaaaaa aaaaaaaaaa aaaaaaaaa   1020
aaaaaag                                                           1027
```

<210> SEQ ID NO 4
<211> LENGTH: 248
<212> TYPE: PRT
<213> ORGANISM: Zea mays

<400> SEQUENCE: 4

```
Thr Arg Pro Ala Leu Leu Ser Arg Leu Ile Glu Ser Leu Pro Ala Asp
  1               5                  10                  15

Ala Glu Ser Leu Ile Lys Trp Val Val Glu Val Arg Arg Lys Glu Glu
             20                  25                  30

Gly Gly Pro Ser Leu Asn Lys Glu Glu Lys Glu Arg Leu Phe Leu Lys
         35                  40                  45

Glu Asn Val Leu Lys Gln Val Arg Asp Thr Arg Leu Phe Thr Ile Val
     50                  55                  60

His Asp Leu Gln Tyr Ala Asn Lys Pro Cys Tyr Asn Cys Ser Ser Ser
 65                  70                  75                  80

Ser Glu Asp Asp Ser Leu Thr Arg Ile Ala Ala Val Val Cys Cys Gln
                 85                  90                  95

Gly Ala Ala Met Leu Ser Gly Asn Leu Val Pro Arg Asp Ala Phe Cys
            100                 105                 110

Cys Arg Glu Thr Ser Phe Glu Cys Val Gln Ala Asn Gly Asp Gly Leu
        115                 120                 125

Lys Thr Val Ile Ser Gly Ser Val Val Cys Glu Gly Ser Glu Gln Gly
    130                 135                 140

Val Asp Met Leu Leu Pro Met Ser Ser Pro Gly Ala Ser Ser Cys Asn
145                 150                 155                 160
```

```
Ser Asn Leu Lys Ser Asn Ala Val Lys Tyr Pro Ser Ser Val Asp Val
            165                 170                 175

Leu Thr Val Leu Leu Ala Leu His Pro Asn Thr Trp Leu Gly Ile
        180                 185                 190

Lys Asp Glu Lys Leu Lys Ala Glu Phe Gln Thr Leu Ile Ser Thr Asp
            195                 200                 205

Ser Leu Pro Asp Asp Leu Lys Arg Glu Ile Leu His Leu Arg Arg Gln
        210                 215                 220

Leu Tyr Tyr Leu Lys Ala Cys Lys Glu Glu Glu Cys Glu Asp Ala Glu
225                 230                 235                 240

Gln Pro Ser Pro Lys Gln Gln Cys
                245

<210> SEQ ID NO 5
<211> LENGTH: 642
<212> TYPE: DNA
<213> ORGANISM: Oryza sativa

<400> SEQUENCE: 5
gcacgagccg atatccacat tggaaacaag cgtgtgcaat tcaaattcaa gcaacgaggt      60
tgtcaaatat ccatctagaa cagatatttt aactgttcta ttgctggctt tacatcctag     120
cacatgggtg gcattaaaag acgagaggct gaaagctgaa ttccagagtc ttatttcaac     180
agacattctt catgatgatc ttaaacgaga gatattgcat ctaagacggc aactccatta     240
tgtgaggtcc tgtaaagagg aggaatatgg agatcctgtg ccacaatccc attaacaatg     300
atgcaaatcg cgcagttggt taccctggag atgcaaaaaa aagggggttag aggaggaact     360 acatactccg tattaccttt gtttcgagtg aggacttctc attttttgaga cacctgacct     420 gagacggatc cgtgtagaca tgttcatgtt catcacctgt ggtcgtttct cttgttagtg     480
acaactgaca actagcgggg aggcacacgc taattgtgcg gctggtgtcc ttgcaaaagt     540
ttctcataat aacgcaatgg cagatatatt ttcacacttt attattaaat aaaaatattg     600
aaaagggcaa ttaaggagta ggataaaaaa aaaaaaaaaa aa                        642

<210> SEQ ID NO 6
<211> LENGTH: 97
<212> TYPE: PRT
<213> ORGANISM: Oryza sativa

<400> SEQUENCE: 6

His Glu Pro Ile Ser Thr Leu Glu Thr Ser Val Cys Asn Ser Asn Ser
1               5                   10                  15

Ser Asn Glu Val Val Lys Tyr Pro Ser Arg Thr Asp Ile Leu Thr Val
            20                  25                  30

Leu Leu Ala Leu His Pro Ser Thr Trp Val Gly Ile Lys Asp Glu
        35                  40                  45

Arg Leu Lys Ala Glu Phe Gln Ser Leu Ile Ser Thr Asp Ile Leu His
50                  55                  60

Asp Asp Leu Lys Arg Glu Ile Leu His Leu Arg Arg Gln Leu His Tyr
65                  70                  75                  80

Val Arg Ser Cys Lys Glu Glu Glu Tyr Gly Asp Pro Val Pro Gln Ser
                85                  90                  95

His

<210> SEQ ID NO 7
<211> LENGTH: 1469
```

```
<212> TYPE: DNA
<213> ORGANISM: Oryza sativa

<400> SEQUENCE: 7
gcacgagact tccgccacca tctcgtccgc tctgcctcct cccaggactg ccatctcatc      60
gcatcctacc acaggaagcc tttcaaacag actggaaccg gccatttctc tccaatcggc     120
ggctaccatg ccggccaaga catggcgctt atcctggatg tcgcccgctt caaatacccct    180
cctcactggg ttccactccc actgctttgg gaagccatga atacaactga tgacgcaact     240
ggtctactca gggggttcat gcttatctca aggcacactg cagctccttc attgctctac     300
acagtgagtt gcagagatga aagctggaaa agcatggcga agtattgcat ggaagatgta     360
cccgatcttc ttaaggatga gagtgtagac aatgttccag cacttctgtc ccgcttagtg     420
aaatcccttc ctgccaatgc tggaaatttg atcaaatggg ttattgaagt taggagacaa     480
gaggaaggag gatcaggatt aagcaaagag gaggaagaaa ggcttatttt gaaggaaatg     540
atactacagc aagtccgtga tactgagctt tttagattag tccgtgaact gcaattcact     600
aagcagccat gttgtagttg ctcatattca agtgatgatg attcctttac ccggattgca     660
gcctctgtgt gctgtcaagg ggccgcattg ctaacaggga tctttcatc aaaagatggg      720
ttctgctgca gagaaacttg cttcaaatgt gtacaagtgg atggtgatgg gcctaagact     780
gtcgttacag gcacagcggt tcaggagtc aatgaacaaa gtgttgatat gcttctaccg      840
atatccacat tggaaacaag cgtgtgcaat tcaaattcaa gcaacgaggt tgtcaaatat     900
ccatctagaa cagatatttt aactgttcta ttgctggctt tacatcctag cacatgggtg     960
ggcattaaag acgagaggct gaaagctgaa ttccagagtc ttatttcaac agacattctt    1020
catgatgatc ttaaacgaga gatattgcat ctaagacggc aactccatta tgtgaggtcc    1080
tgtaaagagg aggaatatgg agatcctgtg ccacaatccc attaacaatg atgcaaatcg    1140
cgcagttggt tacccctggag atgcaaaaaa aaggggttag aggaggaact acatactccg    1200
tattaccttt gtttcgagtg aggacttctc attttttgaga cacctgaccct gagacggatc    1260
cgtgtagaca tgttcatgtt catcacctgt ggtcgtttct cttgttagtg acaactgaca    1320
actagcgggg aggcacacgc taattgtgcg gctggtgtcc ttgcaaaagt ttctcataat    1380
aacgcaatgg cagatatatt ttcacacttt attattaaat aaaaatattg aaagggcaa     1440
ttaaggagta aaaaaaaaaa aaaaaaaa                                       1469

<210> SEQ ID NO 8
<211> LENGTH: 374
<212> TYPE: PRT
<213> ORGANISM: Oryza sativa

<400> SEQUENCE: 8

Ala Arg Asp Phe Arg His His Leu Val Arg Ser Ala Ser Ser Gln Asp
 1               5                  10                  15

Cys His Leu Ile Ala Ser Tyr His Arg Lys Pro Phe Lys Gln Thr Gly
            20                  25                  30

Thr Gly His Phe Ser Pro Ile Gly Gly Tyr His Ala Gly Gln Asp Met
        35                  40                  45

Ala Leu Ile Leu Asp Val Ala Arg Phe Lys Tyr Pro Pro His Trp Val
    50                  55                  60

Pro Leu Pro Leu Leu Trp Glu Ala Met Asn Thr Thr Asp Asp Ala Thr
65                  70                  75                  80

Gly Leu Leu Arg Gly Phe Met Leu Ile Ser Arg His Thr Ala Ala Pro
```

```
                        85                  90                  95
Ser Leu Leu Tyr Thr Val Ser Cys Arg Asp Glu Ser Trp Lys Ser Met
            100                 105                 110
Ala Lys Tyr Cys Met Glu Asp Val Pro Asp Leu Leu Lys Asp Glu Ser
            115                 120                 125
Val Asp Asn Val Pro Ala Leu Leu Ser Arg Leu Val Lys Ser Leu Pro
            130                 135                 140
Ala Asn Ala Gly Asn Leu Ile Lys Trp Val Ile Glu Val Arg Arg Gln
145                 150                 155                 160
Glu Glu Gly Gly Ser Gly Leu Ser Lys Glu Glu Glu Arg Leu Ile
                165                 170                 175
Leu Lys Glu Met Ile Leu Gln Gln Val Arg Asp Thr Glu Leu Phe Arg
            180                 185                 190
Leu Val Arg Glu Leu Gln Phe Thr Lys Gln Pro Cys Cys Ser Cys Ser
            195                 200                 205
Tyr Ser Ser Asp Asp Asp Ser Phe Thr Arg Ile Ala Ala Ser Val Cys
            210                 215                 220
Cys Gln Gly Ala Ala Leu Leu Thr Gly Asn Leu Ser Ser Lys Asp Gly
225                 230                 235                 240
Phe Cys Cys Arg Glu Thr Cys Phe Lys Cys Val Gln Val Asp Gly Asp
                245                 250                 255
Gly Pro Lys Thr Val Val Thr Gly Thr Ala Val Ser Gly Val Asn Glu
            260                 265                 270
Gln Ser Val Asp Met Leu Leu Pro Ile Ser Thr Leu Glu Thr Ser Val
            275                 280                 285
Cys Asn Ser Asn Ser Ser Asn Glu Val Val Lys Tyr Pro Ser Arg Thr
290                 295                 300
Asp Ile Leu Thr Val Leu Leu Ala Leu His Pro Ser Thr Trp Val
305                 310                 315                 320
Gly Ile Lys Asp Glu Arg Leu Lys Ala Glu Phe Gln Ser Leu Ile Ser
                325                 330                 335
Thr Asp Ile Leu His Asp Asp Leu Lys Arg Glu Ile Leu His Leu Arg
            340                 345                 350
Arg Gln Leu His Tyr Val Arg Ser Cys Lys Glu Glu Glu Tyr Gly Asp
            355                 360                 365
Pro Val Pro Gln Ser His
    370
```

<210> SEQ ID NO 9
<211> LENGTH: 967
<212> TYPE: DNA
<213> ORGANISM: Glycine max

<400> SEQUENCE: 9

```
tttttttttt tttttttttt tatagaaaaa gcaaatgctt ttattcaaga gaaacaactg    60
tgcattacat ttgatactgc tctcaggact atcaagaaca agagcatca tcatacagtt    120
gacgaaggtg actgcaaagg tgatgtcaag acagccaatt tttcagcaaa aaaaaaaaa    180
aaaaactcga gactagttct ccaggtttat accgcagagt gctcccatct ccttcaatcg    240
agttcgcttc gccggaaggg aagaagctgt cggtgaagc gcttgagcga ggaaccatgc    300
aaggcttctt caagctaatt tcatactacc agacacagtc agagcctgca tactgtggcc    360
tcgccactct ttccgttgtc ctcaatgccc ttgccattga ccctggaagg aaatggaaag    420
gtccttggag atggtttgac gagtccatgt tggattgctg tgagcctttg gccaaggtta    480
```

-continued

```
aattggaagg cattacgttc ggtaaagttg catgcttggc tcgatgtaat ggagctaagg    540
ttgaagcctt tcgatcggat caaagctctg ttgatgattt tcgcaaccgt gtgatttcgt    600
gctcttcttc tgaggattgt catgtgattg tgtcttacca caggacaccc ctcaatcaga    660
ctggaattgg ccattttca ccagttggag gatatcatgc tgagagagat atggtccttg     720
ttttggatgt cgctcgtttc aagtatccgc tcactgggt tccccttacc cttctctggg     780
aaggcatgag caccattgat caagcaacca gacttcgtag ggggtacatg attatttcga    840
ggcttaacag agcaccatct atactttata ctgtgagttg tagacatgaa ggttggagca    900
gtgttgccaa atttctaacc gaagatgtcc ctcaacttct aaagtcagag gatctaaaag    960
ctcgtgc                                                              967
```

```
<210> SEQ ID NO 10
<211> LENGTH: 274
<212> TYPE: PRT
<213> ORGANISM: Glycine max

<400> SEQUENCE: 10

Cys Gln Asp Ser Gln Phe Phe Ser Lys Lys Lys Lys Lys Leu Glu
  1               5                  10                  15

Thr Ser Ser Pro Gly Leu Tyr Arg Arg Val Leu Pro Ser Pro Ser Ile
             20                  25                  30

Glu Phe Ala Ser Pro Glu Gly Lys Lys Leu Phe Gly Glu Ala Leu Glu
         35                  40                  45

Arg Gly Thr Met Gln Gly Phe Phe Lys Leu Ile Ser Tyr Tyr Gln Thr
     50                  55                  60

Gln Ser Glu Pro Ala Tyr Cys Gly Leu Ala Thr Leu Ser Val Val Leu
 65                  70                  75                  80

Asn Ala Leu Ala Ile Asp Pro Gly Arg Lys Trp Lys Gly Pro Trp Arg
                 85                  90                  95

Trp Phe Asp Glu Ser Met Leu Asp Cys Cys Glu Pro Leu Ala Lys Val
            100                 105                 110

Lys Leu Glu Gly Ile Thr Phe Gly Lys Val Ala Cys Leu Ala Arg Cys
        115                 120                 125

Asn Gly Ala Lys Val Glu Ala Phe Arg Ser Asp Gln Ser Ser Val Asp
    130                 135                 140

Asp Phe Arg Asn Arg Val Ile Ser Cys Ser Ser Ser Glu Asp Cys His
145                 150                 155                 160

Val Ile Val Ser Tyr His Arg Thr Pro Leu Asn Gln Thr Gly Ile Gly
                165                 170                 175

His Phe Ser Pro Val Gly Gly Tyr His Ala Glu Arg Asp Met Val Leu
            180                 185                 190

Val Leu Asp Val Ala Arg Phe Lys Tyr Pro Pro His Trp Val Pro Leu
        195                 200                 205

Thr Leu Leu Trp Glu Gly Met Ser Thr Ile Asp Gln Ala Thr Arg Leu
    210                 215                 220

Arg Arg Gly Tyr Met Ile Ile Ser Arg Leu Asn Arg Ala Pro Ser Ile
225                 230                 235                 240

Leu Tyr Thr Val Ser Cys Arg His Glu Gly Trp Ser Ser Val Ala Lys
                245                 250                 255

Phe Leu Thr Glu Asp Val Pro Gln Leu Leu Lys Ser Glu Asp Leu Lys
            260                 265                 270

Ala Arg
```

<210> SEQ ID NO 11
<211> LENGTH: 2087
<212> TYPE: DNA
<213> ORGANISM: Helianthus sp.

<400> SEQUENCE: 11

| | | | | | |
|---|---|---|---|---|---|
| gcacgaggaa | ctactctttt | ttgaaaccgt | ttacttccgc | gggttctcct | gatccaacga | 60 |
| gcccaataag | aaacaagtca | gttgatatct | tagatcagtt | cagtaatgac | gacgactatg | 120 |
| gcgactatat | acagaagagt | tcttccatcc | cctcctgcta | ttgatttcgt | ttcttctcaa | 180 |
| ggaaagcaat | tgttcatgga | agccactcaa | ggtggaacaa | tggaaggctt | ctttaagtta | 240 |
| atctcttact | ttcagacaca | atcagaaccc | gcttattgtg | gattggctac | ccttgcaatg | 300 |
| gtcttgaatg | ctctttctat | tgatcctggt | agaaaatgga | aggtccctg | gaggtggttt | 360 |
| gatgaatcta | tgctggattg | ttgtgagcct | tggaaacgg | ttaaagccaa | aggcatttct | 420 |
| tttgggaaag | ttgtttgttt | ggctcattgt | gctggagcaa | agttgaggc | ttttcgcaca | 480 |
| aatcaaacta | gcatcgatga | atttcgcaag | catgttgtag | cctgctctag | ttctgatgac | 540 |
| tgtcatgtca | ttgcttcgta | taacagagcc | actttcaaac | agacgggtgc | tggccacttt | 600 |
| tcgcctatcg | gtggttatca | tgcgggaaga | gatatggtat | taatattaga | gttgcgcgt | 660 |
| tttaaatatc | ctcctcactg | ggtgccactt | aaattacttt | gggaagccat | ggatactgtg | 720 |
| gatcaagcta | gtggatatca | cagaggtttt | atgctggtat | ccaggcttca | acgaccacca | 780 |
| gcattactat | atacctgag | ttgtaagcat | gagagttggg | ttaatatcgc | aaagtacttg | 840 |
| actgaggatg | ttccggagtt | attgagttct | aagaatgtga | aggacgtgaa | agatgttctc | 900 |
| tccattgttt | ttagttcttt | gccatccaag | tttcttgaat | ttattacgtg | ggttccggaa | 960 |
| gttcgaagaa | cagaagaggg | tgatcaaagt | ttaactccag | aagagcaaga | aaggctttcc | 1020 |
| atcaaggggg | agatactgaa | acaggttcag | gagactgaac | tatacaagta | cgtcgcagat | 1080 |
| tttctcgact | ctccatgttc | gggtcaagaa | gccagtttga | ccgagattgc | agcaagtgtg | 1140 |
| tgttgtcagg | gagcaggatt | tttaaaagga | aacagtgaat | cgtctgacgg | attttgctgc | 1200 |
| ggggaaacac | aagtacattg | cataaaaaac | aatggagcca | tgccacatgt | tacgatagtc | 1260 |
| tcggggactg | tgaccaatgg | catcggtgaa | caacatgtgg | atatgttggt | cccttcgtta | 1320 |
| actaatcgca | ttgggttgca | cccagctagc | agtgatgttc | tcatagcact | tttactggcg | 1380 |
| ttaccaccgc | aaatttggtc | cggtatcaaa | gatgatacc | tgttgcggga | aattgatacc | 1440 |
| cttgtttcta | tggataacct | tcctactttg | cttcaagaag | aggttatgca | cttgcgtagt | 1500 |
| cagctctaca | ttctcaagcg | atgcaaagat | aatgaattag | agaaagatct | ttctgcaccc | 1560 |
| ttatagcatc | ctaataccgt | ctggacctcc | atacttcttg | ttacaacttc | aaacgctttc | 1620 |
| tcctactaaa | aagggcagaa | taacacaatg | ttacaactta | caacaattgc | tatgtatgta | 1680 |
| tctgcatcta | ttcccgtctg | tcttttaggt | caattatcaa | gtaagaaacg | atgtattcag | 1740 |
| gagatcaaaa | ccggttcttg | acaagtcaag | attgttatca | ccgggccaac | aacttgctga | 1800 |
| gaggtctgaa | acgccagatc | ggcttttggg | tgggatcagg | cacattattt | attacatggc | 1860 |
| ctaaacgaat | tgcttataca | tcatacatgg | gttcaagatc | tatattttct | tctaattatt | 1920 |
| tatctcatta | aggaagttat | aggatttgtt | ttactgtaat | gctaccaggc | tatgatcgta | 1980 |
| gctgtttagc | gccaacatgc | aataaggaaa | cacacaaact | gtttgtactt | tgtttattta | 2040 |
| aagtagatgg | aatacatagt | ttattctggc | aaaaaaaaaa | aaaaaa | | 2087 |

<210> SEQ ID NO 12
<211> LENGTH: 486
<212> TYPE: PRT
<213> ORGANISM: Helianthus sp.

<400> SEQUENCE: 12

```
Met Thr Thr Thr Met Ala Thr Ile Tyr Arg Arg Val Leu Pro Ser Pro
  1               5                  10                  15

Pro Ala Ile Asp Phe Val Ser Ser Gln Gly Lys Gln Leu Phe Met Glu
             20                  25                  30

Ala Thr Gln Gly Gly Thr Met Glu Gly Phe Phe Lys Leu Ile Ser Tyr
         35                  40                  45

Phe Gln Thr Gln Ser Glu Pro Ala Tyr Cys Gly Leu Ala Thr Leu Ala
     50                  55                  60

Met Val Leu Asn Ala Leu Ser Ile Asp Pro Gly Arg Lys Trp Lys Gly
 65                  70                  75                  80

Pro Trp Arg Trp Phe Asp Glu Ser Met Leu Asp Cys Cys Glu Pro Leu
                 85                  90                  95

Glu Thr Val Lys Ala Lys Gly Ile Ser Phe Gly Lys Val Val Cys Leu
            100                 105                 110

Ala His Cys Ala Gly Ala Lys Val Glu Ala Phe Arg Thr Asn Gln Thr
        115                 120                 125

Ser Ile Asp Glu Phe Arg Lys His Val Val Ala Cys Ser Ser Ser Asp
    130                 135                 140

Asp Cys His Val Ile Ala Ser Tyr Asn Arg Ala Thr Phe Lys Gln Thr
145                 150                 155                 160

Gly Ala Gly His Phe Ser Pro Ile Gly Gly Tyr His Ala Gly Arg Asp
                165                 170                 175

Met Val Leu Ile Leu Asp Val Ala Arg Phe Lys Tyr Pro Pro His Trp
            180                 185                 190

Val Pro Leu Lys Leu Leu Trp Glu Ala Met Asp Thr Val Asp Gln Ala
        195                 200                 205

Ser Gly Tyr His Arg Gly Phe Met Leu Val Ser Arg Leu Gln Arg Pro
    210                 215                 220

Pro Ala Leu Leu Tyr Thr Leu Ser Cys Lys His Glu Ser Trp Val Asn
225                 230                 235                 240

Ile Ala Lys Tyr Leu Thr Glu Asp Val Pro Glu Leu Leu Ser Ser Lys
                245                 250                 255

Asn Val Lys Asp Val Lys Asp Val Leu Ser Ile Val Phe Ser Ser Leu
            260                 265                 270

Pro Ser Lys Phe Leu Glu Phe Ile Thr Trp Val Pro Glu Val Arg Arg
        275                 280                 285

Thr Glu Glu Gly Asp Gln Ser Leu Thr Pro Glu Glu Gln Glu Arg Leu
    290                 295                 300

Ser Ile Lys Gly Glu Ile Leu Lys Gln Val Gln Glu Thr Glu Leu Tyr
305                 310                 315                 320

Lys Tyr Val Ala Asp Phe Leu Asp Ser Pro Cys Ser Gly Gln Glu Ala
                325                 330                 335

Ser Leu Thr Glu Ile Ala Ala Ser Val Cys Cys Gln Gly Ala Gly Phe
            340                 345                 350

Leu Lys Gly Asn Ser Glu Ser Ser Asp Gly Phe Cys Cys Gly Glu Thr
        355                 360                 365

Gln Val His Cys Ile Lys Asn Asn Gly Ala Met Pro His Val Thr Ile
    370                 375                 380
```

Val Ser Gly Thr Val Thr Asn Gly Ile Gly Glu Gln His Val Asp Met
385                 390                 395                 400

Leu Val Pro Ser Leu Thr Asn Arg Ile Gly Leu His Pro Ala Ser Ser
            405                 410                 415

Asp Val Leu Ile Ala Leu Leu Ala Leu Pro Pro Gln Ile Trp Ser
            420                 425                 430

Gly Ile Lys Asp Asp Thr Leu Leu Arg Glu Ile Asp Thr Leu Val Ser
            435                 440                 445

Met Asp Asn Leu Pro Thr Leu Leu Gln Glu Glu Val Met His Leu Arg
    450                 455                 460

Ser Gln Leu Tyr Ile Leu Lys Arg Cys Lys Asp Asn Glu Leu Glu Lys
465                 470                 475                 480

Asp Leu Ser Ala Pro Leu
            485

<210> SEQ ID NO 13
<211> LENGTH: 2020
<212> TYPE: DNA
<213> ORGANISM: Zea mays

<400> SEQUENCE: 13

```
gcacgagccg ggttctgtgg gctctcgtcc atcgtgcccg tcgtcgtctg cagagattcg    60
aaacgaaagt gagagagcat cgcagaggaa aggaggcacc cttcgctggc tcgatcgccg   120
ctgtgttcac gcggaggaac tagatcagca cgcgaaagcc aacagcgcag tcgaggagga   180
agcgagcagt ccaggtccag gatggcggcg gccgtggcgt cgctgtacag gcgggtcctc   240
ccgtcgccgc cggcggtgga cttcgcttcg ccggagggca agcgcctatt cgcggaggcc   300
ctggcggcgg gcaccatgga gggtttcttc cccctggtct ccgtcttcca gacgcagtcg   360
gagccggcct tctgcggcct ggcctcccct gccgtcgtgc tcaacgcgct cgccatcgac   420
ccgggccgcc gctggaaggg gccctggcgg tggttcgacg agtccatgct cgactgctgc   480
gagcccctcg ataaggtcaa ggccgagggc atcaccttcg gcaaggtcgc ctgtctcgcg   540
cactgctccg gagccgacgt ccaatccttc cgcaccaacc gggttaccat ccacgaccta   600
cggcggcatc tcatccgatg cgtctcctcg caggactgcc atctgatcgc ctcctaccac   660
aggcggcctt tcggacagac tggaactggt catttctccc caattggtgg ctaccatgcc   720
ggacaggata tggtgctcat cttggatgtc gcccgtttca aatatcctcc gcattgggtt   780
ccattgcaac ttctttggga agccatgaat acaactgatg actcaactgg acttctcaga   840
gggttcatgc ttatatcaag aaaggttgca gccccttcat tgttgtacac agtgagttgc   900
agagatgaaa actggaaacg catgtcaaaa tattgtgttg aagatttacc gagtcttctg   960
aaggcaggga acctagacga tgttccagcg cttctgtccc gtttaattga gtctcttcca  1020
gctgacgctg aatctttgat caaatgggtt gtcgaagtca ggagaaaaga ggagggtgga  1080
ccaagcttaa acaaagagga gaaagaaagg cttttcttga aggaaaatgt actaaagcaa  1140
gttcgtgata ccaggctatt tgccatagtc catgatttgc agtatgctaa taaaccatgt  1200
tataattgct catcgccgag cgaagatgat tcccttacta ggattgcagc cgttgtgtgc  1260
tgtcagggag ctgcaatgct atcaggtaac cttgtgccaa gagatgcctt ctgctgcaga  1320
gaaacaagct ttgaatgtgt ccaagcgaat ggtgacgggc ttaagactgt tatctcaggc  1380
tccgtggtat gtgaaggcag tgaacaaggt gttgatatgc ttttaccaat gtcttcacct  1440
ggtgccagtt catgcaattc aaacttgaaa agcaatgccg tcaaatatcc atcaagcgtg  1500
```

-continued

```
gatgttctaa ctgttcttct gctggcttta catcccaaca cgtggttggg catcaaagac      1560
gagaagctga aagctgaatt tcagactctt atttcaacag acagtttacc tgatgatctg      1620
aaacgagaga tattgcatct aaggcggcaa ctctactatc taaaggcctg taaagaagag      1680
gaatgcgaag atgccagca accatcgcct aagcagcagt gctgaagtgg cagtgtgccc       1740
atgtcgttag ttttacttgt aagaaattga tgtgaaggga aaagttacca gagggtatag      1800
actatgaaat ggtcagaatt atgatgatag tagtgtagtg atgattatct tgttgttcag      1860
ttctggtgtt gtttccttct acgagaggct attacaccct ccttgctcaa ggaggtgcta      1920
atgttctttt tctagatgat gattaaacca tccatccatc cttgcttgct ttgtgctaaa      1980
aaaaaaaaaa aaaaaaaaaa aaaaaaaaaa aaaaaaaaa                             2020
```

<210> SEQ ID NO 14
<211> LENGTH: 507
<212> TYPE: PRT
<213> ORGANISM: Zea mays

<400> SEQUENCE: 14

```
Met Ala Ala Val Ala Ser Leu Tyr Arg Arg Val Leu Pro Ser Pro
 1               5                  10                  15

Pro Ala Val Asp Phe Ala Ser Pro Glu Gly Lys Arg Leu Phe Ala Glu
                20                  25                  30

Ala Leu Ala Ala Gly Thr Met Glu Gly Phe Phe Pro Leu Val Ser Val
            35                  40                  45

Phe Gln Thr Gln Ser Glu Pro Ala Phe Cys Gly Leu Ala Ser Leu Ala
        50                  55                  60

Val Val Leu Asn Ala Leu Ala Ile Asp Pro Gly Arg Arg Trp Lys Gly
    65                  70                  75                  80

Pro Trp Arg Trp Phe Asp Glu Ser Met Leu Asp Cys Cys Glu Pro Leu
                85                  90                  95

Asp Lys Val Lys Ala Glu Gly Ile Thr Phe Gly Lys Val Ala Cys Leu
               100                 105                 110

Ala His Cys Ser Gly Ala Asp Val Gln Ser Phe Arg Thr Asn Arg Val
           115                 120                 125

Thr Ile His Asp Leu Arg Arg His Leu Ile Arg Cys Val Ser Ser Gln
       130                 135                 140

Asp Cys His Leu Ile Ala Ser Tyr His Arg Arg Pro Phe Gly Gln Thr
145                 150                 155                 160

Gly Thr Gly His Phe Ser Pro Ile Gly Gly Tyr His Ala Gly Gln Asp
               165                 170                 175

Met Val Leu Ile Leu Asp Val Ala Arg Phe Lys Tyr Pro Pro His Trp
           180                 185                 190

Val Pro Leu Gln Leu Leu Trp Glu Ala Met Asn Thr Thr Asp Asp Ser
       195                 200                 205

Thr Gly Leu Leu Arg Gly Phe Met Leu Ile Ser Arg Lys Val Ala Ala
   210                 215                 220

Pro Ser Leu Leu Tyr Thr Val Ser Cys Arg Asp Glu Asn Trp Lys Arg
225                 230                 235                 240

Met Ser Lys Tyr Cys Val Glu Asp Leu Pro Ser Leu Leu Lys Ala Gly
               245                 250                 255

Asn Leu Asp Asp Val Pro Ala Leu Leu Ser Arg Leu Ile Glu Ser Leu
           260                 265                 270

Pro Ala Asp Ala Glu Ser Leu Ile Lys Trp Val Val Glu Val Arg Arg
```

-continued

```
                275                 280                 285
Lys Glu Glu Gly Gly Pro Ser Leu Asn Lys Glu Lys Glu Arg Leu
    290                 295                 300
Phe Leu Lys Glu Asn Val Leu Lys Gln Val Arg Asp Thr Arg Leu Phe
305                 310                 315                 320
Ala Ile Val His Asp Leu Gln Tyr Ala Asn Lys Pro Cys Tyr Asn Cys
                325                 330                 335
Ser Ser Pro Ser Glu Asp Ser Leu Thr Arg Ile Ala Ala Val Val
                340                 345                 350
Cys Cys Gln Gly Ala Ala Met Leu Ser Gly Asn Leu Val Pro Arg Asp
                355                 360                 365
Ala Phe Cys Cys Arg Glu Thr Ser Phe Glu Cys Val Gln Ala Asn Gly
    370                 375                 380
Asp Gly Leu Lys Thr Val Ile Ser Gly Ser Val Val Cys Glu Gly Ser
385                 390                 395                 400
Glu Gln Gly Val Asp Met Leu Leu Pro Met Ser Ser Pro Gly Ala Ser
                405                 410                 415
Ser Cys Asn Ser Asn Leu Lys Ser Asn Ala Val Lys Tyr Pro Ser Ser
                420                 425                 430
Val Asp Val Leu Thr Val Leu Leu Ala Leu His Pro Asn Thr Trp
                435                 440                 445
Leu Gly Ile Lys Asp Glu Lys Leu Lys Ala Glu Phe Gln Thr Leu Ile
    450                 455                 460
Ser Thr Asp Ser Leu Pro Asp Asp Leu Lys Arg Glu Ile Leu His Leu
465                 470                 475                 480
Arg Arg Gln Leu Tyr Tyr Leu Lys Ala Cys Lys Glu Glu Cys Glu
                485                 490                 495
Asp Ala Glu Gln Pro Ser Pro Lys Gln Gln Cys
                500                 505

<210> SEQ ID NO 15
<211> LENGTH: 1951
<212> TYPE: DNA
<213> ORGANISM: Oryza sativa

<400> SEQUENCE: 15
gtcaaatcta tcaatcagct tcagccaaag ccgagagccc cccaaaaga gagagaagca        60 cgcatccgat cgccggcgac gaccgaatct gtgccgggcg gcaggaagga gagcggcgat      120
ggcagcgatg gcatccctgt accggcgtgt ccttccttcg ccgccggctg tggagttcgc      180
gtcggaggag gggaagcggc tgttctcgga ggccctggag agcgggacct tgcaaggctt      240
cttcaacctc atctccgtgt ccagacgca gtcggagccg gccttctgcg gcctcgcctc      300
cctctccgtc gtcctcaacg ccctcgccat cgacccgggc cgccaatgga agggcccctg      360
gaggtggttc gacgagtcca tgcttgactg ctgcgagccc ctcgacaagg tgaaggcgga      420
gggcatcacc ttcgccaaac tcgcctgcct cgcgcactgc gccggtgcca atgtccgctc      480
cttccgcgcc gaccagtcca ccatccacga cttccgccac catctcgtcc gctctgcctc      540
ctcccaggac tgccatctca tcgcatccta ccacaggaag cctttcaaac agactggaac      600
cggccatttc tctccaatcg gcggctacca tgccggccaa gacatggcgc ttatcctgga      660
tgtcgcccgc ttcaaatacc ctcctcactg ggttccactc ccactgcttt gggaagccat      720
gaatacaact gatgacgcaa ctggtctact caggggggttc atgcttatct caaggcacac      780
tgcagctcct tcattgctct acacagtgag ttgcagagat gaaagctgga aaagcatggc      840
```

```
gaagtattgc atggaagatg tacccgatct tcttaaggat gagagtgtag acaatgttcc      900
agcacttctg tcccgcttag tgaaatccct tcctgccaat gctggaaatt tgatcaaatg      960
ggttattgaa gttaggagac aagaggaagg aggatcagga ttaagcaaag gaggaagaa      1020
aaggcttatt ttgaaggaaa tgatactaca gcaagtccgt gatactgagc tttttagatt     1080
agtccgtgaa ctgcaattca ctaagcagcc atgttgtagt tgctcatatt caagtgatga     1140
tgattccttt acccggattg cagcctctgt gtgctgtcaa ggggccgcat tgctaacagg     1200
gaatctttca tcaaaagatg ggttctgctg cagagaaact tgcttcaaat gtgtacaagt     1260
ggatggtgat gggcctaaga ctgtcgttac aggcacagcg gtttcaggag tcaatgaaca     1320
aagtgttgat atgcttctac cgatatccac attggaaaca agcgtgtgca attcaaattc     1380
aagcaacgag gttgtcaaat atccatctag aacagatatt ttaactgttc tattgctggc     1440
tttacatcct agcacatggg tgggcattaa agacagagg ctgaaagctg aattccagag      1500
tcttatttca acagacattc ttcatgatga tcttaaacga gagatattgc atctaagacg     1560
gcaactccat tatgtgaggt cctgtaaaga ggaggaatat ggagatcctg tgccacaatc     1620
ccattaacaa tgatgcaaat cgcgcagttg gttaccctgg agatgcaaaa aaagggggtt     1680
agaggaggaa ctacatactc cgtattacct ttgtttcgag tgaggacttc tcattttga      1740
gacacctgac ctgagacgga tccgtgtaga catgttcatg ttcatcacct gtggtcgttt     1800
ctcttgttag tgacaactga caactagcgg ggaggcacac gctaattgtg cggctggtgt     1860
ccttgcaaaa gtttctcata taacgcaat ggcagatata ttttcacact ttattattaa      1920
ataaaaatat tgaaagggc aattaaggag t                                     1951
```

<210> SEQ ID NO 16
<211> LENGTH: 502
<212> TYPE: PRT
<213> ORGANISM: Oryza sativa

<400> SEQUENCE: 16

```
Met Ala Ala Met Ala Ser Leu Tyr Arg Arg Val Leu Pro Ser Pro Pro
  1               5                  10                  15

Ala Val Glu Phe Ala Ser Glu Glu Gly Lys Arg Leu Phe Ser Glu Ala
             20                  25                  30

Leu Glu Ser Gly Thr Leu Gln Gly Phe Phe Asn Leu Ile Ser Val Phe
         35                  40                  45

Gln Thr Gln Ser Glu Pro Ala Phe Cys Gly Leu Ala Ser Leu Ser Val
     50                  55                  60

Val Leu Asn Ala Leu Ala Ile Asp Pro Gly Arg Gln Trp Lys Gly Pro
 65                  70                  75                  80

Trp Arg Trp Phe Asp Glu Ser Met Leu Asp Cys Cys Glu Pro Leu Asp
                 85                  90                  95

Lys Val Lys Ala Glu Gly Ile Thr Phe Ala Lys Leu Ala Cys Leu Ala
            100                 105                 110

His Cys Ala Gly Ala Asn Val Arg Ser Phe Arg Ala Asp Gln Ser Thr
        115                 120                 125

Ile His Asp Phe Arg His His Leu Val Arg Ser Ala Ser Ser Gln Asp
    130                 135                 140

Cys His Leu Ile Ala Ser Tyr His Arg Lys Pro Phe Lys Gln Thr Gly
145                 150                 155                 160

Thr Gly His Phe Ser Pro Ile Gly Gly Tyr His Ala Gly Gln Asp Met
                165                 170                 175
```

Ala Leu Ile Leu Asp Val Ala Arg Phe Lys Tyr Pro Pro His Trp Val
            180                 185                 190

Pro Leu Pro Leu Leu Trp Glu Ala Met Asn Thr Thr Asp Asp Ala Thr
            195                 200                 205

Gly Leu Leu Arg Gly Phe Met Leu Ile Ser Arg His Thr Ala Ala Pro
            210                 215                 220

Ser Leu Leu Tyr Thr Val Ser Cys Arg Asp Glu Ser Trp Lys Ser Met
225                 230                 235                 240

Ala Lys Tyr Cys Met Glu Asp Val Pro Asp Leu Leu Lys Asp Glu Ser
                    245                 250                 255

Val Asp Asn Val Pro Ala Leu Leu Ser Arg Leu Val Lys Ser Leu Pro
            260                 265                 270

Ala Asn Ala Gly Asn Leu Ile Lys Trp Val Ile Glu Val Arg Arg Gln
            275                 280                 285

Glu Glu Gly Gly Ser Gly Leu Ser Lys Glu Glu Glu Arg Leu Ile
            290                 295                 300

Leu Lys Glu Met Ile Leu Gln Gln Val Arg Asp Thr Glu Leu Phe Arg
305                 310                 315                 320

Leu Val Arg Glu Leu Gln Phe Thr Lys Gln Pro Cys Cys Ser Cys Ser
                    325                 330                 335

Tyr Ser Ser Asp Asp Ser Phe Thr Arg Ile Ala Ala Ser Val Cys
            340                 345                 350

Cys Gln Gly Ala Ala Leu Leu Thr Gly Asn Leu Ser Ser Lys Asp Gly
            355                 360                 365

Phe Cys Cys Arg Glu Thr Cys Phe Lys Cys Val Gln Val Asp Gly Asp
            370                 375                 380

Gly Pro Lys Thr Val Val Thr Gly Thr Ala Val Ser Gly Val Asn Glu
385                 390                 395                 400

Gln Ser Val Asp Met Leu Leu Pro Ile Ser Thr Leu Glu Thr Ser Val
                    405                 410                 415

Cys Asn Ser Asn Ser Ser Asn Glu Val Val Lys Tyr Pro Ser Arg Thr
            420                 425                 430

Asp Ile Leu Thr Val Leu Leu Ala Leu His Pro Ser Thr Trp Val
            435                 440                 445

Gly Ile Lys Asp Glu Arg Leu Lys Ala Glu Phe Gln Ser Leu Ile Ser
            450                 455                 460

Thr Asp Ile Leu His Asp Asp Leu Lys Arg Glu Ile Leu His Leu Arg
465                 470                 475                 480

Arg Gln Leu His Tyr Val Arg Ser Cys Lys Glu Glu Glu Tyr Gly Asp
                    485                 490                 495

Pro Val Pro Gln Ser His
            500

<210> SEQ ID NO 17
<211> LENGTH: 1920
<212> TYPE: DNA
<213> ORGANISM: Glycine max

<400> SEQUENCE: 17
tgaacagaga aagattgaag aagaaacaga agaagagaag gttttatttt gcatggcaag      60
tccaggttta taccgcagag tgctcccatc tccttcaatc gagttcgctt cgccggaagg     120
gaagaagctg ttcggtgaag cgcttgagcg aggaaccatg caaggcttct tcaagctaat     180
ttcatactac cagacacagt cagagcctgc atactgtggc ctcgccactc tttccgttgt     240

-continued

```
cctcaatgcc cttgccattg accctggaag gaaatggaaa ggtccttgga gatggtttga      300
cgagtccatg ttggattgct gtgagccttt ggccaaggtt aaattggaag cattacgtt       360
cggtaaagtt gcatgcttgg ctcgatgtaa tggagctaag gttgaagcct ttcgatcgga      420
tcaaagctct gttgatgatt ttcgcaaccg tgtgatttcg tgctcttctt ctgaggattg      480
tcatgtgatt gtgtcttacc acaggacacc cctcaatcag actggaattg gccattttc       540
accagttgga ggatatcatg ctgagagaga tatggtcctt gttttggatg tcgctcgttt      600
caagtatccg cctcactggg ttccccttac ccttctctgg gaaggcatga gcaccattga      660
tcaagcaacc agacttcgta gggggtacat gattatttcg aggcttaaca gagcaccatc      720
tatactttat actgtgagtt gtagacatga aggttggagc agtgttgcca aatttctaac      780
cgaagatgtc cctcaacttc taaagtcaga ggatctaaaa gacattcagg aagtactctc      840
tcttgctttt aaatctcctc ccagtgaatt gagagggtta ataacatgga ttgctgaagt      900
tcgcaggcaa gaagatggga atctcacact gagtgaggag gagaaaggaa ggctagctat      960
caaggctgac atactggaac agattcgaac aactggactc ttcaaacacg tgacaaggtg     1020
gttggattct gaaagttcat gttgtaatac tttagcaaac cttggtgaca agatatgtt      1080
accagcactt gctgccagtg tttgttgcca agcggcagat cttttgactg tttgtggtag     1140
gctaggtttg tcaggtggaa aatgctgtag tcaaatagat gtaaaacatc tgaatgctga     1200
tagtgaaaat ccagtaacat tagttttcag aattgttaca actggtggtg gtagtgaaca     1260
aggagttgat gtgttggtcc ctttgtgtca aagggaacca gtaggttgt gtctttctaa      1320
tgaaggtcac tgcattggca tgcacccgtc tactgcagat gtcttaacgg tgcttttatt     1380
ggccttgccc ttgcatacgt ggtctggcat taaagaagaa aagctgcgtg tggaagcttt     1440
gagccttcta gcaacagaag atctccctcc cctacttcag gaagagggttt tgttcttgcg     1500
agaccaactc cattttctca tgactgatat cagtgctcct tctccctcat gatactattg     1560
tctatcagtt ttgactaatg taacgggttc ctacaatacg atgacattag actgttttag     1620
catcaggtgt gtccttgaac ttggaatcaa tacagcatta gcattgctgt ggtgctatgt     1680
tgaacacgtc aaaaaacaac tacagttgta cctttgggca agaaatttag acaacataat     1740
tgtgtatgga aagaatatca tgcggatttg cataatctgt tgatggaaga tgaggataat     1800
catcggaatg tactaaaaca atttgggtct gataatttgg acaaacattt atatatgaag     1860
aaaataagaa aaatgaaata aacttattca aaagctaaaa aaaaaaaaaa aaaaaaaaa      1920
```

<210> SEQ ID NO 18
<211> LENGTH: 499
<212> TYPE: PRT
<213> ORGANISM: Glycine max

<400> SEQUENCE: 18

```
Met Ala Ser Pro Gly Leu Tyr Arg Arg Val Leu Pro Ser Pro Ser Ile
 1               5                   10                  15

Glu Phe Ala Ser Pro Glu Gly Lys Lys Leu Phe Gly Glu Ala Leu Glu
            20                  25                  30

Arg Gly Thr Met Gln Gly Phe Phe Lys Leu Ile Ser Tyr Tyr Gln Thr
        35                  40                  45

Gln Ser Glu Pro Ala Tyr Cys Gly Leu Ala Thr Leu Ser Val Val Leu
    50                  55                  60

Asn Ala Leu Ala Ile Asp Pro Gly Arg Lys Trp Lys Gly Pro Trp Arg
65                  70                  75                  80
```

-continued

```
Trp Phe Asp Glu Ser Met Leu Asp Cys Cys Glu Pro Leu Ala Lys Val
                 85                  90                  95
Lys Leu Glu Gly Ile Thr Phe Gly Lys Val Ala Cys Leu Ala Arg Cys
            100                 105                 110
Asn Gly Ala Lys Val Glu Ala Phe Arg Ser Asp Gln Ser Ser Val Asp
        115                 120                 125
Asp Phe Arg Asn Arg Val Ile Ser Cys Ser Ser Glu Asp Cys His
130                 135                 140
Val Ile Val Ser Tyr His Arg Thr Pro Leu Asn Gln Thr Gly Ile Gly
145                 150                 155                 160
His Phe Ser Pro Val Gly Gly Tyr His Ala Glu Arg Asp Met Val Leu
                165                 170                 175
Val Leu Asp Val Ala Arg Phe Lys Tyr Pro Pro His Trp Val Pro Leu
            180                 185                 190
Thr Leu Leu Trp Glu Gly Met Ser Thr Ile Asp Gln Ala Thr Arg Leu
        195                 200                 205
Arg Arg Gly Tyr Met Ile Ile Ser Arg Leu Asn Arg Ala Pro Ser Ile
210                 215                 220
Leu Tyr Thr Val Ser Cys Arg His Glu Gly Trp Ser Ser Val Ala Lys
225                 230                 235                 240
Phe Leu Thr Glu Asp Val Pro Gln Leu Leu Lys Ser Glu Asp Leu Lys
                245                 250                 255
Asp Ile Gln Glu Val Leu Ser Leu Ala Phe Lys Ser Pro Pro Ser Glu
            260                 265                 270
Leu Arg Gly Leu Ile Thr Trp Ile Ala Glu Val Arg Arg Gln Glu Asp
        275                 280                 285
Gly Asn Leu Thr Leu Ser Glu Glu Lys Gly Arg Leu Ala Ile Lys
290                 295                 300
Ala Asp Ile Leu Glu Gln Ile Arg Thr Thr Gly Leu Phe Lys His Val
305                 310                 315                 320
Thr Arg Trp Leu Asp Ser Glu Ser Ser Cys Cys Asn Thr Leu Ala Asn
                325                 330                 335
Leu Gly Asp Lys Asp Met Leu Pro Ala Leu Ala Ser Val Cys Cys
            340                 345                 350
Gln Ala Ala Asp Leu Leu Thr Val Cys Gly Arg Leu Gly Leu Ser Gly
        355                 360                 365
Gly Lys Cys Cys Ser Gln Ile Asp Val Lys His Leu Asn Ala Asp Ser
370                 375                 380
Glu Asn Pro Val Thr Leu Val Ser Gly Ile Val Thr Thr Gly Gly Gly
385                 390                 395                 400
Ser Glu Gln Gly Val Asp Val Leu Val Pro Leu Cys Gln Arg Glu Pro
                405                 410                 415
Ser Arg Leu Cys Leu Ser Asn Glu Gly His Cys Ile Gly Met His Pro
            420                 425                 430
Ser Thr Ala Asp Val Leu Thr Val Leu Leu Ala Leu Pro Leu His
        435                 440                 445
Thr Trp Ser Gly Ile Lys Glu Glu Lys Leu Arg Val Glu Ala Leu Ser
        450                 455                 460
Leu Leu Ala Thr Glu Asp Leu Pro Pro Leu Gln Glu Glu Val Leu
465                 470                 475                 480
Phe Leu Arg Asp Gln Leu His Phe Leu Met Thr Asp Ile Ser Ala Pro
                485                 490                 495
```

Ser Pro Ser

<210> SEQ ID NO 19
<211> LENGTH: 500
<212> TYPE: PRT
<213> ORGANISM: Triticum aestivum

<400> SEQUENCE: 19

```
Met Glu Val Ala Ser Leu Tyr Arg Arg Val Leu Pro Ser Pro Pro Ala
 1               5                  10                  15

Val Glu Phe Ala Ser Ala Glu Gly Lys Arg Leu Phe Ala Glu Ala Leu
            20                  25                  30

Gln Gly Gly Thr Met Glu Gly Phe Phe Asn Leu Ile Ser Tyr Phe Gln
        35                  40                  45

Thr Gln Ser Glu Pro Ala Phe Cys Gly Leu Ala Ser Leu Ser Val Val
    50                  55                  60

Leu Asn Ala Leu Ala Ile Asp Pro Gly Arg Pro Trp Lys Gly Pro Trp
65                  70                  75                  80

Arg Trp Phe Asp Glu Ser Met Leu Asp Cys Cys Glu Pro Leu His Lys
                85                  90                  95

Val Lys Ala Glu Gly Ile Thr Phe Gly Lys Val Val Cys Leu Ala His
            100                 105                 110

Cys Ala Gly Ala Arg Val Gln Ser Phe Arg Ala Asp Gln Thr Thr Ile
        115                 120                 125

His Asp Phe Arg Ala His Leu Thr Arg Cys Ala Ser Ser Gln Asp Cys
    130                 135                 140

His Leu Ile Ser Ser Tyr His Arg Ser Pro Phe Lys Gln Thr Gly Thr
145                 150                 155                 160

Gly His Phe Ser Pro Ile Gly Gly Tyr His Ala Glu Lys Asp Met Ala
                165                 170                 175

Leu Ile Leu Asp Val Ala Arg Phe Lys Tyr Pro Pro His Trp Val Pro
            180                 185                 190

Leu Thr Leu Leu Trp Asp Ala Met Asn Thr Thr Asp Glu Ala Thr Gly
        195                 200                 205

Leu Leu Arg Gly Phe Met Leu Val Ser Arg Arg Ser Ser Ala Pro Ser
    210                 215                 220

Leu Leu Tyr Thr Val Ser Cys Gly His Gly Ser Trp Lys Ser Met Ala
225                 230                 235                 240

Lys Tyr Cys Val Glu Asp Val Pro Asn Leu Leu Lys Asp Glu Ser Leu
                245                 250                 255

Asp Asn Val Thr Thr Leu Leu Ser Arg Leu Val Glu Ser Leu Pro Ala
            260                 265                 270

Asn Ala Gly Asp Leu Ile Lys Cys Val Ile Glu Val Arg Arg Lys Glu
        275                 280                 285

Glu Gly Glu Ser Ser Leu Ser Lys Glu Glu Lys Glu Arg Leu Phe Leu
    290                 295                 300

Lys Glu Lys Val Leu Gln Gln Ile Arg Asp Thr Asp Leu Phe Arg Val
305                 310                 315                 320

Val His Glu Leu Gln Tyr Pro Lys Gly Leu Cys Gly Ser Cys Ser Ser
                325                 330                 335

Ser Ser Asp Glu Asp Ser Leu Ala Glu Ile Ala Ala Thr Val Cys Cys
            340                 345                 350

Gln Gly Ala Ala Phe Leu Ser Gly Asn Leu Val Ser Arg Asp Gly Phe
        355                 360                 365
```

-continued

```
Cys Cys Arg Glu Thr Cys Ile Lys Cys Ile Glu Ala Asn Gly Asp Gly
        370                 375                 380

Leu Lys Thr Val Ile Ser Gly Thr Val Val Ser Lys Gly Asn Glu Gln
385                 390                 395                 400

Ala Val Asp Leu Leu Pro Thr Ser Ser Ser Lys Thr Ser Leu Cys
                405                 410                 415

Asn Ser Asn Leu Lys Ser Lys Ile Val Lys Tyr Pro Ser Ser Thr Asp
            420                 425                 430

Val Leu Thr Val Leu Leu Val Leu Gln Pro Asn Thr Trp Leu Gly
                435                 440                 445

Ile Lys Asp Glu Asn Val Lys Ala Glu Phe Gln Ser Leu Val Ser Thr
450                 455                 460

Asp Asn Leu Pro Asp Leu Leu Lys Gln Glu Ile Leu His Leu Arg Arg
465                 470                 475                 480

Gln Leu His Tyr Leu Ala Gly Cys Lys Gly Gln Glu Ala Cys Gln Glu
                485                 490                 495

Pro Pro Ser Pro
            500

<210> SEQ ID NO 20
<211> LENGTH: 485
<212> TYPE: PRT
<213> ORGANISM: Arabidopsis thaliana

<400> SEQUENCE: 20

Met Ala Met Ala Ser Leu Tyr Arg Arg Ser Leu Pro Ser Pro Pro Ala
1               5                   10                  15

Ile Asp Phe Ser Ser Ala Glu Gly Lys Leu Ile Phe Asn Glu Ala Leu
            20                  25                  30

Gln Lys Gly Thr Met Glu Gly Phe Phe Arg Leu Ile Ser Tyr Phe Gln
        35                  40                  45

Thr Gln Ser Glu Pro Ala Tyr Cys Gly Leu Ala Ser Leu Ser Val Val
    50                  55                  60

Leu Asn Ala Leu Ser Ile Asp Pro Gly Arg Lys Trp Lys Gly Pro Trp
65                  70                  75                  80

Arg Trp Phe Asp Glu Ser Met Leu Asp Cys Cys Glu Pro Leu Glu Val
                85                  90                  95

Val Lys Glu Lys Gly Ile Ser Phe Gly Lys Val Val Cys Leu Ala His
            100                 105                 110

Cys Ser Gly Ala Lys Val Glu Ala Phe Arg Thr Ser Gln Ser Thr Ile
        115                 120                 125

Asp Asp Phe Arg Lys Phe Val Val Lys Cys Thr Ser Ser Glu Asn Cys
    130                 135                 140

His Met Ile Ser Thr Tyr His Arg Ser Val Phe Lys Gln Thr Gly Asn
145                 150                 155                 160

Gly His Phe Ser Pro Ile Gly Gly Tyr Asn Ala Glu Arg Asp Met Ala
                165                 170                 175

Leu Ile Leu Asp Val Ala Arg Phe Lys Tyr Pro Pro His Trp Val Pro
            180                 185                 190

Leu Lys Leu Leu Trp Glu Ala Met Asp Ser Ile Asp Gln Ser Thr Gly
        195                 200                 205

Lys Arg Arg Gly Phe Met Leu Ile Ser Arg Pro His Arg Glu Pro Gly
    210                 215                 220

Leu Leu Tyr Thr Leu Ser Cys Lys Asp Glu Ser Trp Ile Glu Ile Ala
225                 230                 235                 240
```

```
Lys Tyr Leu Lys Glu Asp Val Pro Arg Leu Val Ser Ser Gln His Val
                245             250             255

Asp Ser Val Glu Lys Ile Ile Ser Val Val Phe Lys Ser Leu Pro Ser
                260             265             270

Asn Phe Asn Gln Phe Ile Arg Trp Val Ala Glu Ile Arg Ile Thr Glu
                275             280             285

Asp Ser Asn Gln Asn Leu Ser Ala Glu Glu Lys Ser Arg Leu Lys Leu
                290             295             300

Lys Gln Leu Val Leu Lys Glu Val His Glu Thr Glu Leu Phe Lys His
305                 310             315                 320

Ile Asn Lys Phe Leu Ser Thr Val Gly Tyr Glu Asp Ser Leu Thr Tyr
                325             330             335

Ala Ala Ala Lys Ala Cys Cys Gln Gly Ala Glu Ile Leu Ser Gly Ser
                340             345             350

Pro Ser Lys Glu Phe Cys Cys Arg Glu Thr Cys Val Lys Cys Ile Lys
                355             360             365

Gly Pro Asp Asp Ser Glu Gly Thr Val Val Thr Gly Val Val Val Arg
    370             375             380

Asp Gly Asn Glu Gln Lys Val Asp Leu Leu Val Pro Ser Thr Gln Thr
385                 390             395                 400

Glu Cys Glu Cys Gly Pro Glu Ala Thr Tyr Pro Ala Gly Asn Asp Val
                405             410             415

Phe Thr Ala Leu Leu Leu Ala Leu Pro Pro Gln Thr Trp Ser Gly Ile
                420             425             430

Lys Asp Gln Ala Leu Met His Glu Met Lys Gln Leu Ile Ser Met Ala
                435             440             445

Ser Leu Pro Thr Leu Leu Gln Glu Glu Val Leu His Leu Arg Arg Gln
    450             455             460

Leu Gln Leu Leu Lys Arg Cys Gln Glu Asn Lys Glu Glu Asp Asp Leu
465                 470             475                 480

Ala Ala Pro Ala Tyr
                485

<210> SEQ ID NO 21
<211> LENGTH: 8
<212> TYPE: PRT
<213> ORGANISM: Artificial Sequence
<220> FEATURE:
<223> OTHER INFORMATION: Consensus motif in isoprenylated metal-binding
      proteins

<400> SEQUENCE: 21

Phe Ser Glu Asp Asn Pro Asn Ala
  1               5
```